US008005526B2

(12) United States Patent
Martin et al.

(10) Patent No.: US 8,005,526 B2
(45) Date of Patent: Aug. 23, 2011

(54) BIOLOGICALLY INTEGRATED ELECTRODE DEVICES

(75) Inventors: David C. Martin, Ann Arbor, MI (US); Sarah Richardson-Burns, Ypsilanti, MI (US); Donghwan Kim, Ann Arbor, MI (US); Jeffrey L. Hendricks, Ann Arbor, MI (US); Laura Povlich, Taylor, MI (US); Mohamad Reza Abidian, Ann Arbor, MI (US); Matthew Meier, Ann Arbor, MI (US)

(73) Assignee: The Regents of The University of Michigan, Ann Arbor, MI (US)

( * ) Notice: Subject to any disclaimer, the term of this patent is extended or adjusted under 35 U.S.C. 154(b) by 1348 days.

(21) Appl. No.: 11/512,479

(22) Filed: Aug. 30, 2006

(65) Prior Publication Data

US 2007/0060815 A1 Mar. 15, 2007

Related U.S. Application Data

(60) Provisional application No. 60/713,070, filed on Aug. 31, 2005.

(51) Int. Cl.
*A61B 5/04* (2006.01)
*A61N 1/05* (2006.01)

(52) U.S. Cl. ........ 600/372; 600/377; 600/378; 607/116; 607/137

(58) Field of Classification Search .................. 600/372, 600/377, 378

See application file for complete search history.

(56) References Cited

U.S. PATENT DOCUMENTS

| | | | | |
|---|---|---|---|---|
| 4,341,221 A | | 7/1982 | Testerman | |
| 4,585,652 A | | 4/1986 | Miller et al. | |
| 5,031,621 A | | 7/1991 | Grandjean et al. | |
| 5,092,332 A | | 3/1992 | Lee et al. | |
| 5,130,412 A | | 7/1992 | Wellinghoff et al. | |
| 5,368,028 A | * | 11/1994 | Palti | 600/345 |
| 5,513,636 A | * | 5/1996 | Palti | 600/352 |
| 6,095,148 A | | 8/2000 | Shastri et al. | |
| 6,132,752 A | | 10/2000 | Pickett et al. | |
| 6,179,835 B1 | | 1/2001 | Panescu et al. | |
| 6,197,881 B1 | | 3/2001 | Cosnier | |
| 6,294,245 B1 | | 9/2001 | Roitman et al. | |
| 6,331,244 B1 | | 12/2001 | Lewis et al. | |
| 6,468,304 B1 | | 10/2002 | Dubois-Rande et al. | |
| 6,627,154 B1 | | 9/2003 | Goodman et al. | |
| 6,696,575 B2 | | 2/2004 | Schmidt et al. | |
| 6,730,212 B1 | | 5/2004 | Yamagishi et al. | |
| 6,890,715 B1 | | 5/2005 | Lewis et al. | |

(Continued)

OTHER PUBLICATIONS

Campbell et al., "Incorporation of Erythrocytes into Polypyrrole to Form the Basis of a Biosensor to Screen for Rhesus (D) Blood Groups and Rhesus (D) Antibodies," Electroanalysis, 11, No. 4 (1999), pp. 215-222.

(Continued)

*Primary Examiner* — Lee S Cohen
(74) *Attorney, Agent, or Firm* — Harness, Dickey & Pierce, P.L.C.

(57) ABSTRACT

Bioelectrodes having enhanced biocompatible and biomimetic features are provided. Methods of making and using the bioelectrodes are further provided. A biologically integrated bioelectrode device and method for detecting electronic signals using a bioelectrode comprising a first electrically conductive substrate and a biological component. The bioelectrode also comprises a conductive polymer electrically coupling the first electrically conductive substrate and the biological component to define a bioelectrode. The bioelectrode can transmit or receive an electrical signal between the electrically conductive substrate and the biological component and conductive polymer.

29 Claims, 5 Drawing Sheets

Figure 1A:
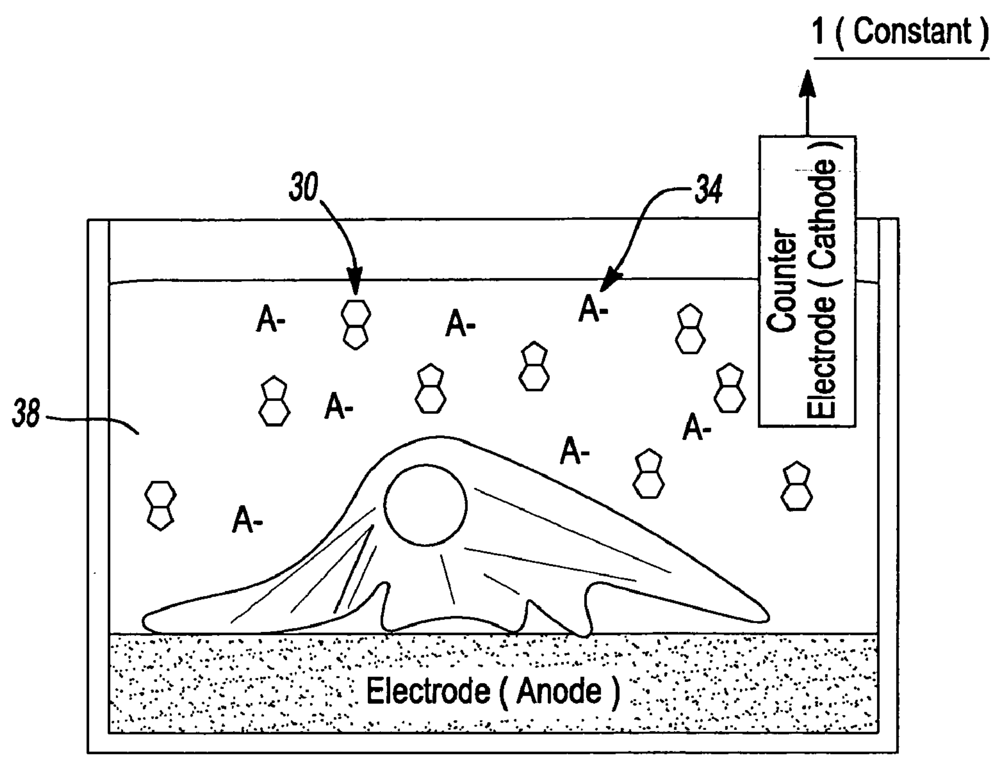

90
100
120
100
130
110

U.S. PATENT DOCUMENTS

| | | | | |
|---|---|---|---|---|
| 7,045,205 | B1 | 5/2006 | Sager | |
| 7,070,592 | B2 | 7/2006 | Santini, Jr. et al. | |
| 2005/0033132 | A1 | 2/2005 | Shults et al. | |
| 2005/0048651 | A1 | 3/2005 | Ryttsen et al. | |
| 2005/0121068 | A1 | 6/2005 | Sager et al. | |
| 2005/0234513 | A1* | 10/2005 | Alexander et al. | 607/2 |
| 2005/0263394 | A1 | 12/2005 | Lewis et al. | |
| 2006/0160100 | A1 | 7/2006 | Gao et al. | |
| 2007/0073130 | A1* | 3/2007 | Finch et al. | 600/372 |

OTHER PUBLICATIONS

Cui et al., "In vivo studies of polypyrrole/peptide coated neural probes," Biosensors and Bioactuators B 89 (2003), pp. 92-102.

Khor et al., "In situ polymerization of pyrrole in animal tissue in the formation of hybrid biomaterials," Biomaterials, vol. 16, No. 8 (1995), pp. 657-661.

Rahman et al., "The biosensor based on the pyruvate oxidase modified conducting polymer for phsophate ions determinations," The Biosensors and Bioactuators 21 (2006), pp. 1116-1124.

Schmidt et al., "Stimulation of neurite outgrowth using an electrically conducting polymer," Applied Biological Sciences, Proc. Natl. Acad. Sci USA, vol. 94 (Aug. 1997), pp. 8948-8953.

Cui et al., "Electrochemical deposition and characterization of conducting polymer polypyrrole/PSS on multichannel neural probes," Sensor and Actuators A 93 (2001) 8-18.

Cui et al., "Electrochemical deposition and characterization of poly(3,4-ethylenedioxythiophene) on neural microelectrode arrays," Sensor and Actuators A 89 (2003) 92-102.

Yang et al., "Ordered surfactant-templated poly(3,4-ethylenedioxythiophene) (PEDOT) conducting polymer on microfabricated neural probes," Acta Biomaterialia 1 (2005) 125-136.

Nyberg et al., "Polymer Hydrogel Microelectrodes for Neural Communication," Biomedical Microdevices 4:1, 43-52, (2002).

Gilmore et al., "Preparation of Hydrogel/Conducting Polymer Composites," Polymer Gels and Networks 2 (1994) 135-143.

Ghosh et al., "Electrochemical Characterization of Poly(3,4-ethylene dioxythiophene) Based Conducting Hydrogel Networks," Journal of The Electrochemical Society, 147 (5) 1872-1877 (2000).

Kim et al, "Electroformation of conducting polymers in a hydrogel support matrix," Polymer 41 (2000) 1783-1790.

Woerly, "Restorative surgery of the central nervous system by means of tissue engineering using NeuroGel implants," Neurosurg Rev (2000) 23:59-77.

Xiao et al., "Electrochemical polymerization of poly(hyrdoxmethylated-3,4-ethlenedioxythiophene) (PEDOT-MeOH) on multichannel neural probes," Sensors and Actuators B 99 (2004) 437-443.

Gooding et al., "Electrochemical modulation of antigen-antibody binding," Biosensors and Bioelectronics 20 (2004) 260-268.

Kositsky et al., "Dynamical Dimension of a Hybrid Neurorobotic System," IEEE Transactions on Neural Systems and Rehabilitation Engineering, vol. 11, No. 2, p. 155, Jun. 2002.

Kipke, et al., "Silicon-Substrate Intracortical Microelectrode Arrays for Long-Term Recording of Neuronal Spike Activity in Cerebral Cortex," IEEE Transactions on Neural Systems and Rehabilitation Engineering, vol. 11, No. 2, p. 155, Jun. 2002.

Yang et al., "Microporous conducting polymers on neural microelectrode arrays I Electrochemical deposition," Sensors and Actuators B 101 (2004) 133-142.

Yang et al., "Microporous conducting polymers on neural microelectrode arrays II Physical characterization," Sensors and Actuators A 113 (2004) 204-211.

Kim et al., "Conducting polymers grown in hydrogel scaffolds coated on neural prosthetic devices," 2004 Wiley Periodicals, Inc.

Kim et al., "Incorporation and controlled release of a hydrophilic antibiotic using poly(lactide-co-glycolide)-based electrospun nanofibrous scaffolds," Journal of Controlled Release 98 (2004), 47-56.

Cui et al., "Surface modification of neural recording electrodes with conducting polymer/biomolecule blends," J. Biomed. Mater. Res., 56(2)(2001), pp. 261-272.

Cui X et al: "In vivo studies of polypyrrole/peptide coated neuraal probes" Biomaterials, Elsevier Science Publishers BV., Barking, GB, vol. 24, No. 5, Feb. 1, 2003, pp. 777-787, XP004398696 ISSN: 0142-9612.

Yang J et al: "Ordered surfactant-templated poly (3,4-ethylenedioxythiophene) (PEDOT) conducting polymer on microfabricated neural probes" Acta Biomaterialia, Elsevier, Amsterdam, NL, vol. 1, No. 1, Jan. 1, 2005, pp. 125-136, XP025338297 ISSN: 1742-7061 [retrieved on Jan. 1, 2005].

Supplementary European Search Report mailed Mar. 9, 2010.

* cited by examiner

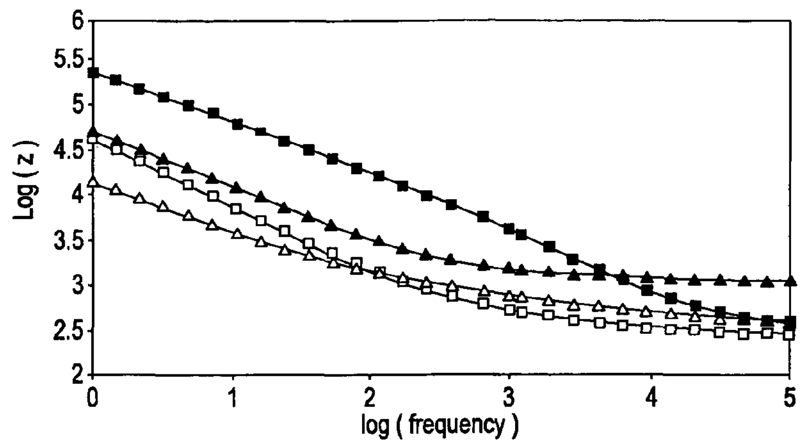

Fig-6A bare AuSS wire in PBS
PEDOT ( EDOT-PBS-PSS;50 uA, 180s ) - coated AuSS wire
PEDOT ( EDOT-PBS-PSS;50 uA, 180s ) - coated AuSS wire in x-link'd 0.5% MVG alignate
GelDOT ( 50 uA, 1800s ) grown off PEDOT ( EDOT-PBS-PSS; 50 uA, 180s ) - coated AuSS wire in x-link'd 0.5% MVG alignate

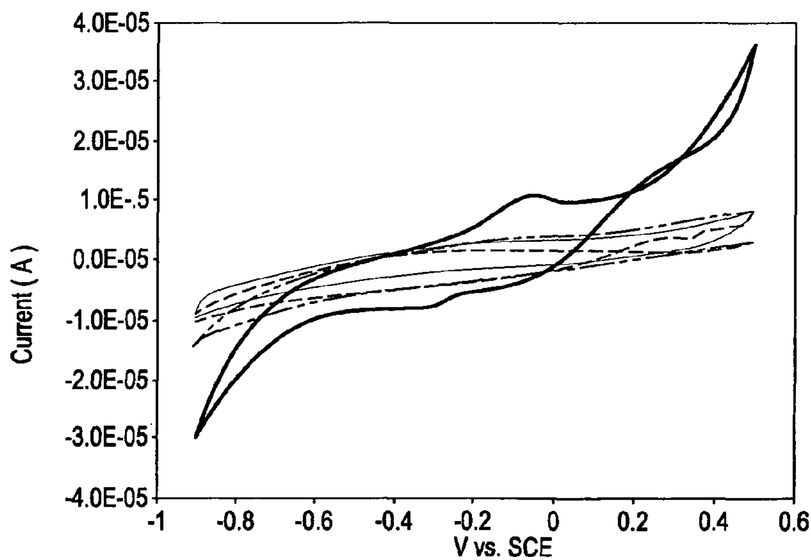

Fig-6B bare AuSS wire in PBS
PEDOT ( EDOT-PBS-PSS; 50 uA, 180s ) - coated AuSS wire
PEDOT ( EDOT-PBS-PSS; 50 uA, 180s ) - coated AuSS wire in x-link'd 0.5% MVG alignate
GelDOT ( 50 uA, 1800s ) grown off PEDOT ( EDOT-PBS-PSS; 50 uA, 180s ) - coated AuSS wire in x-link'd 0.5% MVG alignate

BIOLOGICALLY INTEGRATED ELECTRODE DEVICES

CROSS-REFERENCE TO RELATED APPLICATIONS

This application claims the benefit of U.S. Provisional Application No. 60/713,070, filed on Aug. 31, 2005. The disclosure of the above application is incorporated herein by reference.

GOVERNMENT RIGHTS

This disclosure was made with government support under National Science Foundation Grant No. DMR-0084304 and National Institutes of Health Grant No. N01-NS-1-2338. The Government has certain rights in the invention.

FIELD

The present teachings relates to biocompatible, biologically integrated bioelectrode devices resulting from non-toxic deposition and polymerization of conducting polymers, in the presence of biological components. In particular, the present teachings relates to an apparatus and methods for the detection, stimulation, and recording of electrical, chemical, and ionic interactions between a bioelectrode and various biologic and chemical targets. The methods can be used for the detection and stimulation of charge transfer interactions between a conductive polymer and the surrounding tissue, cells, chemicals, electrolytes, charge carriers receptors and enzymes that are permitted to interact with the bioelectrode.

BACKGROUND

Inherently "conductive polymers" ($\pi$-conjugated conductive polymers) and non-conductive polymers with conductive dopants are useful as biocompatible polymeric coating materials for preexisting electrodes, probes, and sensors providing unique electrical, biochemical and electroactive properties. The monomers that polymerize to form conductive polymers can comprise one or more of 3,4-ethylenedioxythiophene (EDOT), pyrrole, anilines, acetylenes, thiophenes, and blends thereof.

Surface and bulk materials currently used as electrodes for biomedical devices offer limited biocompatibility, resulting in tissue injury and inflammation in the vicinity of the implanted device. In addition to limited biocompatibility, stimulation of chronic negative immune system reactions often lead to biofouling of existing implants of electrodes and erosion of device surface materials. Various biological tissues, including the central nervous system (CNS) react negatively to implanted devices, varying in severity according to the site of implantation, the materials used and differences in electrode geometries and implantation methodologies. Chronic rejection of the implantable devices in the CNS can be characterized by a hypertrophic reaction from surrounding astrocytes with increased expression of filament proteins and vimentin. In addition to protein adsorption to the device surface, microglial cells and foreign body giant cells envelop the implanted devices resulting in encapsulation of the device and formation of high electrical impedance fibrous scar tissue. This diminishes, and eventually negates signal transduction between the tissue and the device. Similar foreign-body responses are found throughout human and animal tissues including major targets for novel implanted biomedical devices including the brain, heart, and skin. Bioincompatibility represents a key weakness of new implantable biomedical devices currently being developed and is the foremost roadblock to successful in vivo testing and usage.

Surface modification of implantable electrodes and sensors should provide improvements in both their long term biocompatibility and eletro-functionality. It would be highly desirable to design electrode devices which could intimately interface electrode sites to living tissue, as well as to facilitate efficient charge transport from ionically conductive tissue to the electronically conductive electrode and induce surrounding tissue to attach or interface directly to the implanted device.

SUMMARY

The present teachings provide a composition for the construction of an electrochemical sensing and stimulation device wherein the electrode is intimately in contact with a biological component during the recordation and stimulating process. An electrically conductive substrate or working electrode is coated with a conductive polymer that can be polymerized as a conductive polymer matrix in the presence of live tissue, cells, cell constituents and in artificial scaffolds which greatly increases the effective surface area of the bioelectrode resulting in lowered impedance and enhanced biocompatibility thereby facilitating signal transduction. The biologically integrated electrode further stabilizes the electrically conductive substrate by interfacing the electrically conductive substrate with surrounding cells and/or tissue when implanted and can be loaded with bioactive substances that prevent the formation of unwanted immune rejections.

A further aspect of the present teachings relates to biologically integrated electrodes comprising a first electrically conductive substrate and a biological component. The bioelectrode also comprises a conductive polymer comprising one or more conductive polymers electrically coupling the first conductive substrate to the biological component to define a bioelectrode. The bioelectrode can transmit or receive an electronic signal between the first electrically conductive substrate and the biological component and conductive polymer.

A further aspect of the present teachings relates to a method of electrically detecting the transfer of charge between or within cells in living tissue. The method includes the steps of providing a bioelectrode device comprising a first electrically conductive substrate or working electrode in intimate contact with tissue capable of transferring electronic charge. The bioelectrode device is made up of a first electrically conductive substrate and a biological component. The bioelectrode also includes a conductive polymer electrically coupling the first electrically conductive substrate to the biological component to collectively define a bioelectrode. The bioelectrode can transmit or receive an electrical signal between the first electrically conductive substrate any one of the biological component and the conductive polymer. The method also includes electrically connecting the bioelectrode device and a second electrically conductive substrate (another electrode) electrically coupled with the bioelectrode to a power source. The method further includes applying a voltage or current across the first and second electrically conductive substrates, thereby inducing a voltage or current across the conductive polymer. The method also detects the transfer of electrical signals with the bioelectrode device.

Further areas of applicability of the present teachings will become apparent from the detailed description provided hereinafter. It should be understood that the detailed description and specific examples, while indicating certain embodiments of the present teachings, are intended for purposes of illustration only and are not intended to limit the scope of the invention.

DRAWINGS

The drawings described herein are for illustration purposes only and are not intended to limit the scope of the present disclosure in any way.

Figure 1B:
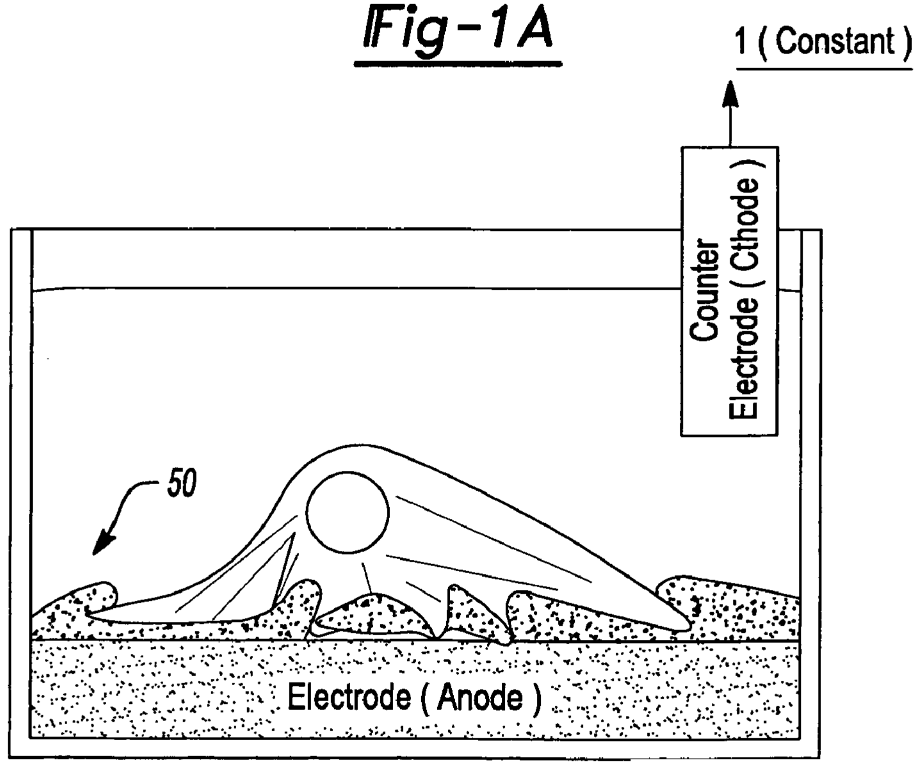

FIGS. 1A and 1B depict illustrations of a cell adhered to a conductive substrate and contacted with a conducting polymer in accordance with the teachings of the present disclosure. FIG. 1A is an illustration depicting an adherent cell on an electrically conductive substrate surface in solution with conducting monomer and corresponding counter ions or dopant prior to application of current and electropolymerization of the conducting monomer into conducting polymer around the substrate and portions of the adherent cell. FIG. 1B is an illustration depicting an adherent cell on an electrically conductive substrate with electrically conductive polymerization of the monomer around the substrate and portions of the adherent cell in accordance with the present disclosure.

Figure 2A:
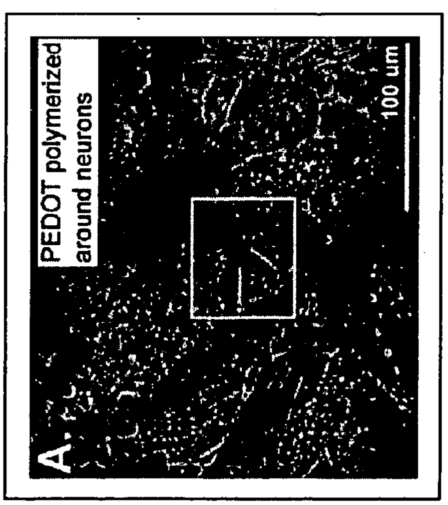
Figure 2B:
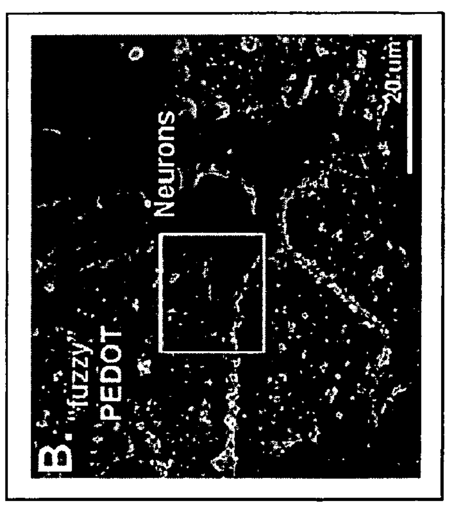
Figure 2C:
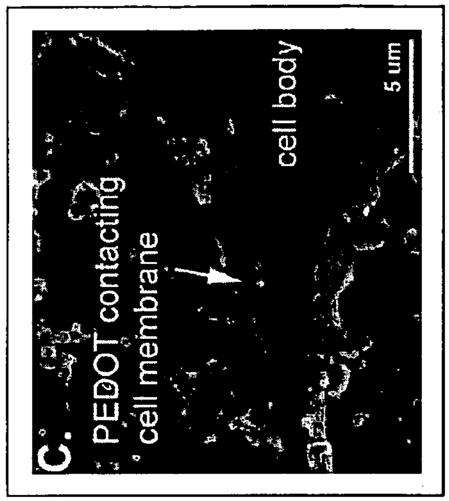

FIGS. 2A-2C depict photomicrographs of scanning electron micrographs of neurons embedded within electropolymerized conducting polymer. FIG. 2A depicts an electron photomicrograph showing a neuron integrated completely and intimately with PEDOT. FIG. 2B is a magnification of FIG. 2A depicting three-dimensional fuzzy electrically conductive polymer around the attached neuron. FIG. 2C depicts a higher magnification of FIG. 2B showing intimate contact of the electrically conductive polymer in contact with neuron processes according to the teachings of the present disclosure.

Figure 3A:
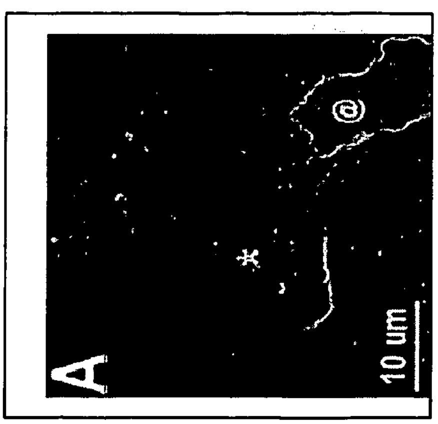
Figure 3B:
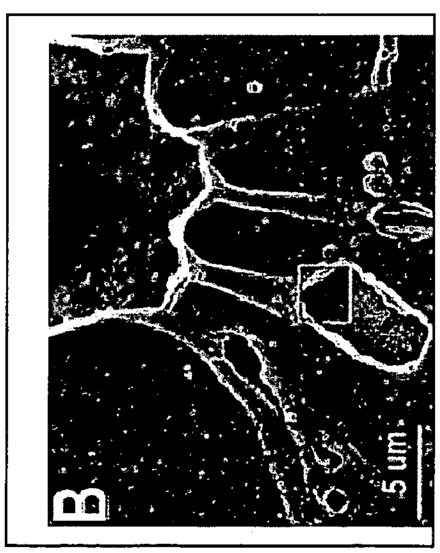
Figure 3C:
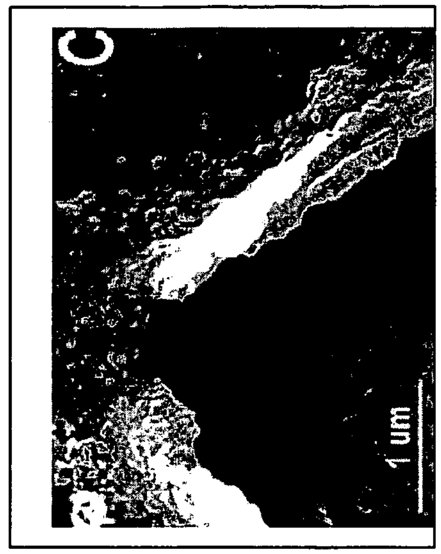

FIGS. 3A-3C depict photomicrographs of electron microscopic examination of templated electrically conductive polymer forming cell-defined polymer topography including cavities and crevices suitable for cellular occupation. FIG. 3A depicts neuron templated tunnels and neurite invaginations on the surface of an electrically conductive substrate. FIG. 3B depicts a magnified neurite outgrowth templated tunnel. FIG. 3C depicts a closer magnification of the conducting polymer templated tunnel according to the teachings of the present disclosure.

Figure 4A:
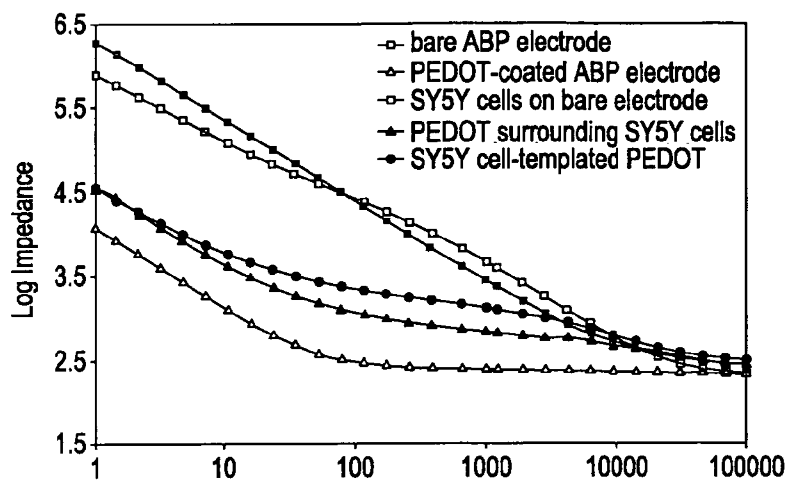
Figure 4B:
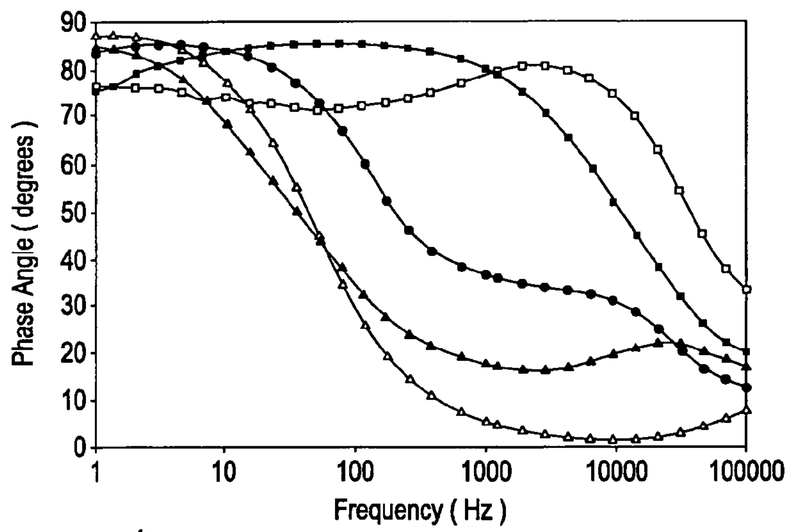
Figure 4C:
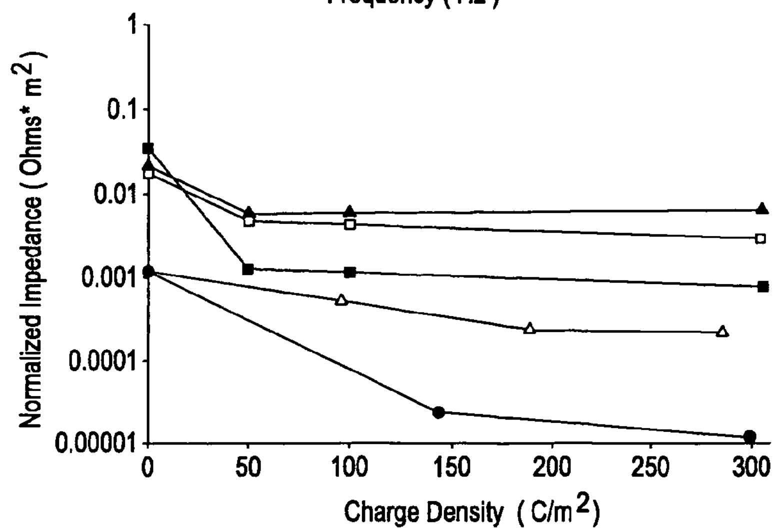

FIGS. 4A-4C are line graphs illustrating the electrochemical characteristics of bare electrodes, electrodes coated with conductive polymer, cell templated conductive polymer and electrodes with adherent cells surrounded by conductive polymer. FIG. 4A depicts the reduction of electrical impedance in electrodes coated with conductive polymer and cells templated and embedded with conductive polymer over bare electrodes. FIG. 4B depicts phase angle reduction in electrodes coated with conductive polymer and cells templated and embedded with conductive polymer over bare electrodes. FIG. 4C depicts normalized impedance over charge density of electrodes coated with conductive polymer in comparison to templated polymer containing and cell embedded electrodes.

Figure 5:
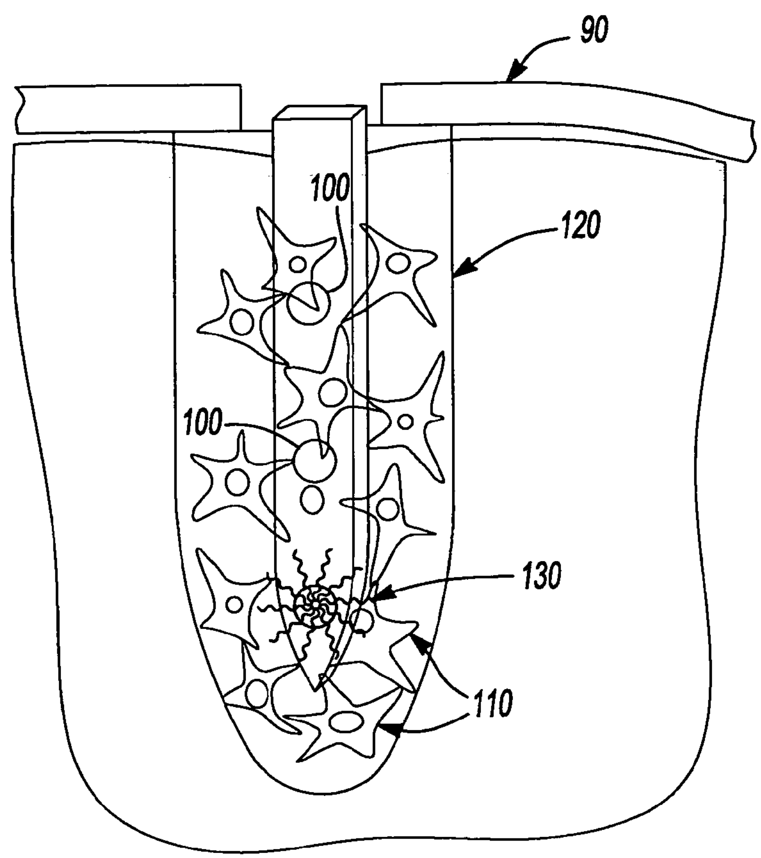

FIG. 5 depicts an illustration of a space-filling electrode according to the teachings of the present disclosure.

FIGS. 6A and 6B depict line graphs of electrode electrochemical characteristics when implanted in hydrogel constructs in cochlea of a living guinea pig in accordance with the present disclosure. FIG. 6A depicts a line graph of electrical impedance over frequency. FIG. 6B depicts a line graph of cyclic voltammetry analysis of electrodes embedded into cochlea of a living guinea pig in accordance with the teachings of the present disclosure.

Figure 7:
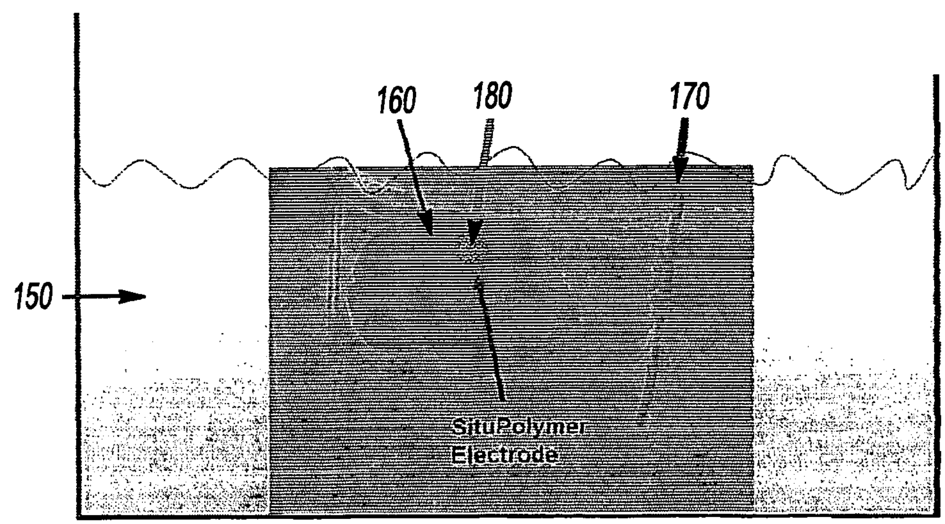

FIG. 7 depicts an illustration of components used to fabricate an in situ bioelectrode device in tissue in accordance with the teachings of the present disclosure.

DETAILED DESCRIPTION

The biocompatible electrodes (bioelectrodes), modified electrodes and coatings contemplated by certain embodiments of the present teachings include electrode devices and/or conductive polymer coatings which have low biodegradability, low electrical impedance, long-term electrical stability under in vivo conditions, are mechanically soft, are highly biomimetic (cell feature/cell surface templated & patterned) with nanometer and micrometer scale surface features. Certain embodiments of the present teachings relate to conducting cell-templated, live cell-seeded bioelectrodes, or molecular electrode networks that can be adapted for any molecular species including, for example: capable of forming conductive macromolecular networks; biocompatible non-toxic and/or non-immunogenic in the polymer or macromolecular state; able to be processed from a water or saline-based solution or gel of monomeric units or small oligomer components into macromolecular or polymeric films or networks by electrochemical or chemical polymerization or crosslinking with either UV/photo, electrical, thermal, chemical, or self-initiation. The resulting electroconductive films and electrode coatings can be mechanically stable to withstand degradation and maintain electrical integrity and connectivity for the duration of implementation.

Devices having macro, micro and nano-scale components can be patterned with such electroconductive polymers polymerized in the presence of biological components including tissue, cells, cellular constituents including, membranes, receptors, antibodies, ion-channels, growth factors and other biological molecules and agents. Bioelectrodes, modified electrodes and electrode coatings of the present teachings impart beneficial features including electrodes and electrode coating materials that are electrically stable over time following implantation in tissue, relatively non-biodegradable yet biocompatible, eliciting lower levels of immuno-reactivity than commonly used conductive substrate materials such as silicon, platinum, iridium, indium tin oxide, and tungsten. The bioelectrodes or electrode coatings of the present teachings can be readily modified to contain a variety of bioactive agents to facilitate interactions with specific proteins or biomolecules on the target cells and can limit non-specific interactions that are associated with device surface biofouling. Proteins can be incorporated into the conducting polymer material via a variety of methods such as electrochemical deposition, covalent linkage, and entrapment in the polymer matrix. Bioelectrodes and devices comprising electrode coatings described herein, can be soft, fuzzy electrodes with low electrical impedance and large surface areas with biomimetic surface patterns (cell-shaped holes and tunnels with cell-surface templated nanoscale features). The large surface area is ideal for facilitating maximal charge transfer between the electrode and target tissue. The pliability of the polymer allows for decreased mechanical strain at the interface between the soft tissue and the hard device surface compared to a rigid metal electrode. Together, these qualities allow the conductive polymer-coated cells, cell components, and bioactive molecules of the present teachings to serve as a high surface area, soft, biocompatible, and electrically stable surface coatings for existing electrode-based biomedical devices that will result in decreased immunoreactivity and improved signal transduction and integration (tissue adhesion) at the interface between the tissue and the device.

In some embodiments, the uses of conducting polymers patterned on the surface of electrically conductive substrates facilitate signal transport from onically conductive tissue to the electronically conductive electrode. Polymerized conducting polymer with a biological component is also referred to herein as a "conducting polymer network" or "hybrid biological component-conducting polymer material" to describe the three dimensional nature of the conductive substrate coating. Certain embodiments of the present teachings provide for novel conducting polymer networks as well as a process for polymerizing conducting polymers in the presence of tissue, cells, cell constituents and other bioactive molecules that result in intimate, direct interfacing between the surface of an electrode-based device and a biological environment.

The detailed description of the present teachings will deal separately with the electrode components, including, electrically conductive substrates, conjugated conducting polymers, biological components, optional instrumentation including controllers and analytical instruments and power sources. Methods of fabricating the various exemplified bioelectrodes and electrodes modified with the biological component embedded conducting polymer coatings and their uses are further described. Finally, the present teachings are exemplified with a number of bioelectrodes and devices and experiments demonstrating the utility and novelty thereof.

A. Device Components and Materials

I. Electrically Conductive Substrates

Electrode substrates can comprise any conducting material or combination of conducting and non-conducting materials. A number of exemplary electrically conductive substrate configurations are described and can be understood that other configurations can be used. In non-limiting embodiments, electrically conductive substrates can be manufactured from metals including, but not limited to: Gold (Au), Platinum (Pt), Iridium (Ir), Palladium (Pd), Tungsten (W), Nickel (Ni), Copper (Cu) Aluminum (Al), Stainless Steel (SS), Indium-Tin-Oxide (ITO), Zinc (Zn), Titanium (Ti), Tungsten (W) and their alloys and oxides. Other electrically conductive substrates can include: carbon, carbon fiber, glassy carbon, carbon composites, carbon paste, conductive ceramics, for example, doped silicon (Si), conductive monomers and polymers. As used herein, the first electrically conductive substrate is the substrate or electrode that is in contact or coupled with the biological component and the conducting polymer. The first electrically conductive substrate can also be referred to as the working electrode in a multi conductive substrate bioelectrode device. The second electrically conductive substrate can also be referred to any one of: the reference electrode, the counter electrode, or the saturated calomel electrode.

In some embodiments, the electrode can be patterned with electrically conducting material such as metal powders, conductive polymers or conductive ceramics. The underlying support material need not necessarily be composed of conducting material, provided that the support material can be made conductive, or that conductive material can be formed or patterned in or on the non-conductive support.

Devices comprising one or more electrode arrays can include any suitable support material upon which a plurality of conducting material channels, dots, spots are formed. In general, if the support material of the electrode is to come into contact with biological fluid, the support should be essentially biocompatible. The microelectrode arrays of the present teachings need not be in any specific shape, that is, the electrodes need not be in a square matrix shape. Contemplated electrode array geometries can include: squares; rectangles; rectilinear and hexagonal grid arrays various polygon boundaries; concentric circle grid geometries wherein the electrodes form concentric circles about a common center, and which may be bounded by an arbitrary polygon; and fractal grid array geometries having electrodes with the same or different diameters. Interlaced electrodes can also be used in accordance with the present teachings. In some embodiments, the array of electrodes can comprise about 9 to about 16 electrodes in a 4×4 matrix, 16 to about 25 electrodes in about a 5×5 matrix, 10 to 100 electrodes in a 10×10 matrix. Other sized arrays known in the art may be used in accordance with the present teachings.

Production of patterned array of microelectrodes can be achieved by a variety of microprinting methodologies commonly known in the production of micro-arrays, including, without limitation, by ejecting a plurality of electro-conducting polymers via a multi-line head nozzle, via ink-jetting techniques and the like. They can be patterned using photolithographic and etching methods known for computer chip manufacture. The micromechanical components may be fabricated using compatible "micromachining" processes that selectively etch away parts of the silicon wafer, or comparable substrate, or add new structural layers to form the mechanical and/or electromechanical components.

Electrodes formed on polymeric supports such as those contemplated in Micro-electro-mechanical systems (MEMS) manufacture can include depositing thin films of conducting material on a support material, applying a patterned mask on top of the films by photolithographic imaging or other known lithographic methods, and selectively etching the films. A thin film may have a thickness in the range of a few nanometers to 100 micrometers. Deposition of electroconducting materials for use as micro or nano electrodes contemplated in the present teachings can also include chemical procedures such as chemical vapor deposition (CVD), electrodeposition, epitaxy and thermal oxidation and physical procedures like physical vapor deposition (PVD) and casting. Methods for manufacture of nano-electromechanical systems having enhanced biocompatible interfaces comprising conducting polymers and biomolecules, including cells and cell constituents may be used for certain embodiments of the present disclosure. (See, for example, Craighead, Science 290: 1532-36, 2000).

In some embodiments of the present teachings, an array or subarrays of conducting polymer comprising one or more cells, cell constituents and/or bioactive molecules on an electrode can be connected to various fluid filled compartments, (including conducting monomer solutions comprising cells, cell constituents, hydrogel and biological molecules), such as microfluidic channels, nanochannels and/or microchannels. These and other components of the apparatus may be formed as a single unit, for example in the form of a chip, microcapillary or microfluidic chips. Various forms of microfabricated chips may be commercially available from, for example, Caliper Technologies Inc. (Mountain View, Calif., USA.) and ACLARA BioSciences Inc. (Mountain View, Calif., USA).

In some embodiments, the degradability of the electrode substrate can be dependent on the function served by the device or electrode. For example, conductive and non-conductive materials with conductive degradable polymers can be synthesized out of materials including PLGA, PLA, HA, biorubber, oxide glass and other biocompatible biodegradable materials known to those skilled in the art. The relevance of such materials is apparent when the function of the device or electrode is to transiently stimulate, regenerate injured or defective tissue and then fade from prevalence after successful implantation to make room for complete regeneration and connectivity of the cells or tissue. In some embodiments, the electrically conductive substrate can be permanent to semi-permanent, wherein the device may be used for extended periods of time or once implanted, it would be deleterious to remove, for example some deep brain neural prosthesis, heart pacemakers and the like. Electrically conductive substrates contemplated for such long-term usage can include metals, ceramics, and non-degradable conducting polymers, for example, PEDOT.

In some embodiments, the electrode can be connected in part or in whole to other device components, including wires, leads, conductive polymers that are in electrical communication with other device components used to measure, record and analyze the flow of current or detect changes in impedance, inductance, resistance or capacitance of the bioelectrode, cell, conducting polymer-cell interface or site of implantation. In various embodiments of the present teachings multiple or a plurality of electrodes in parallel or in series can be used to polymerize the conducting monomer, perform electrochemical oxidation/reduction reactions, provide a current or currents and voltages to stimulate tissue and/or cells, for release of bioactives and for recording or sensing electrochemical events. Other electrodes that can be implemented in the devices described herein can further include various counter electrodes and saturated calomel electrodes or reference electrodes.

II. Conductive Polymer

In certain embodiments of the present teachings, conductive polymers can impart desirable features, for example: are electrically stable over time following implantation in tissue, relatively non-biodegradable yet highly biocompatible, eliciting lower levels of immunoreactivity than commonly used conducting materials such as silicon, platinum, iridium, indium tin oxide, and tungsten. As used herein, conductive polymers are conjugated polymers that are capable of conducting electrons. The term “conductive polymer(s)” is used interchangeably with “conducting polymer(s)”. Conductive polymers are formed from their monomeric form via electrochemical polymerization, oxidative polymerization and other methods commonly used in the art. Conducting polymer polymerized around an electrically conductive substrate can also be referred to as a conducting polymer network due to its three dimensional, fuzzy, soft fibrils that extend out from the electrically conductive substrate. In some embodiments, the conducting polymer network contains embedded biological components including cells, cellular constituents, bioactive molecules or substances and combinations thereof. Conducting polymer networks having one or more biological components are also referred to as hybrid biological component-conducting polymer material. In certain embodiments of the present teachings, the conductive polymers can be polymerized in the presence of dopants, tissue, cells, cell parts, cellular constituents, other bioactive molecules, viral, plasmid, yeast, dendromer, quantum dot, or micro-nano particle gene delivery vectors, and/or biodegradable micro-nano particles or fibers that are comprised of naturally-derived or synthetic polymers that may be decorated with surface functional groups or molecules intended for interaction with specific cells or molecules in the target tissue or may be employed for controlled-release delivery of bioactive molecules contained within.

In some embodiments, the conducting polymers can include, but are not limited to: poly(3,4-ethylenedioxythiophene) (PEDOT), poly(pyrrole), polyanilines, polyacetylenes, poly (diallyldimethylammonium chloride, poly-4-vinylpyridine, poly(vinylalcohol), polythiophenes, polymer blends thereof, and composites with the ability to conduct electronic charge or ions, and hybrid polymer-metal materials that are electrically or ionically conductive. Other conductive polymer can include functionalized copolymers made from EDOT and other conducting polymer derivatives, functional groups such as RGD, IKVAV, YIGSR peptides, and other functional groups that can be covalently attached to the conducting monomer, or they can be linked to spacers having bifunctional moities that can be attach to the conducting monomer. A covalent attachment can be effected using any covalent chemistry known in the art. Examples of preferred covalent attachment chemistries include amine, amide, ester, ether, and their heteroatom cognates, e.g., sulfonamide, thioether, and so forth. Typically, each pair of entities to be joined can jointly comprise a pair of reactive groups, such as a nucleophile and an electrophile, one respectively on each member of the pair. Where the biological entity (biomolecule, cell, cell fragment, organelle, or other biologic) is to be directly attached to the monomer or polymer, each will contain one reactive group of a pair. Where attachment is to take place through a linker, the linker will contain two reactive groups, one of which is capable of covalently reacting with a reactive group of the monomer and the other of which is capable of covalently reacting with a reactive group of the biological entity. The reactive group(s) can be already present as part of the monomer, linker, or biological entity, or it can be added thereto by reaction prior to performing the attachment reaction. Where attachment is to take place through a linker, the linker can be attached first to the polymer, first to the biological entity, or concurrently to both. Non-limiting examples of preferred nucleophile and electrophile groups for use in forming a covalent attachment are presented in Table 1.

Typically, the entities to be covalently attached can be suspended or dissolved in an appropriate solvent, e.g., aqueous methanol, aqueous ethanol, acetonitrile, dimethyl formamide, acetone, dimethyl sulfoxide, or a combination thereof, at an appropriate pH, commonly about pH 7 to about pH 10, and at a temperature from about 10° C. to about 40° C. A neutral-to-basic pH is typically used and this is in most cases provided by addition of a base to the reaction medium. Examples of preferred bases for this purpose include inorganic bases and organic nitrogenous bases. Among inorganic bases, metal hydroxides, carbonates, and bicarbonates are preferred, preferably alkali metal hydroxides, carbonates, and bicarbonates, and combinations thereof. Examples of preferred inorganic bases include sodium carbonate, sodium bicarbonate, sodium hydroxide, potassium carbonate, potassium bicarbonate, lithium hydroxide, lithium carbonate, potassium hydroxide, and combinations thereof.

TABLE 1

Exemplary Reactive Group Pairs For Attachment Chemistries

| Nucleophile | Electrophile | Attachment |
|---|---|---|
| Amine | Alkyl carbodiimide-activated ester | Amide |
| | Bromoacetamide | Amine |
| | Carboxyl | Amide |
| | Chloroacetamide | Amine |
| | Cyclic carboxylic anhydride | Amide |
| | 9-Fluorenylmethoxycarbonyl | Amide |
| | N-Hydroxysuccinimide ester | Amide |
| | Isocyanate | Urea |
| | Isothiocyanate | Thiourea |
| | Phosphate | Phosphoramide |
| | Phosphonate | Phosphonamide |
| | Sulfonate | Sulfonamide |
| Alcohol (or Thiol) | Alkyl carbodiimide-activated ester | Ester (or Thioester) |
| | Bromoacetamide | Ether (or Thioether) |
| | Carboxyl | Ester (or Thioester) |

TABLE 1-continued

Exemplary Reactive Group Pairs For Attachment Chemistries

| Nucleophile | Electrophile | Attachment |
|---|---|---|
| | Chloroacetamide | Ether (or Thioether) |
| | Cyclic carboxylic anhydride | Ester (or Thioester) |
| | Ester | Ester (or Thioester) |
| | 9-Fluorenylmethoxycarbonyl | Ester (or Thioester) |
| | N-Hydroxysuccinimide ester | Ester (or Thioester) |
| | Maleimido | Ester (or Thioester) |
| | Semicarbazido | Ester (or Thioester) |
| | Thiosemicarbazido | Ester (or Thioester) |
| | Alkyl tosylate, mesylate, brosylate, nosylate, nonaflate, triflate, or tresylate salts | Ether (or Thioether) |

In some embodiments, conducting polymers can be any non-conductive monomer or polymer that can be made conductive in the presence of an appropriate doping system. In some embodiments, conjugated polymers described herein can also be chemically synthesized to contain functional side groups that can allow for binding of proteins, lipids and nucleic acids before or after polymerization. In addition to functionalization of the conducting polymers, bioactive molecules, including proteins, lipids and nucleic acids can be also attached to the conductive polymers through hydrogen bonding, electrostatic and non-polar interactions. In some embodiments, the conductive polymer is biodegradable and will dissolve in the presence of biological fluid, for example, when the device is implanted in situ e.g. implantable brain prostheses, neural stimulators, transient heart devices and the like. The biodegradable conducting polymer can include, but is not limited to, polypyrrole poly(3,4-ethylenedioxythiophene) block PEG, and poly(3,4ethylenedioxythiophene), tetramethacrylate and others which are commercially available from TDA Research Inc., Wheat Ridge Colo., USA.

Conductive polymers contemplated by the present teachings typically require counter ions for polymerization and electroconductivity across the electrode-tissue interface. The conducting polymers are reached with a polyelectrolyte at the molecular level. Electron delocalization is a consequence of the presence of conjugated double bonds in the conducting polymer backbone. To make the conducting polymers electrically conductive, it is necessary to introduce mobile carriers into the double bonds, this is achieved by oxidation or reduction reactions (called "doping"). The concept of doping distinguishes conducting polymers from all other kinds of polymers. This process can be assigned as pdoping or n-doping in relation to the positive or negative sign of the injected charge in the polymer chain by analogy to doping in inorganic semiconductors. These charges remain delocalized being neutralized by the incorporation of counter-ions (anions or cations) denominated dopants. In certain embodiments, ionic electrolytes or dopants used to polymerize conducting polymers include but are not limited to: poly(styrene sulfonate) (PSS; Sigma Aldrich, St. Louis, Mo., USA), $LiClO_4$, Phosphate-buffered saline (PBS; HyClone, Logan, UT), Hank's Balanced Salt Solution (HBSS, HyClone), Collagen, Poly-D-Lysine (PDL), Poly-L-Lysine, poly-ornithine, and bioactive molecules of interest having the appropriate ionic charge for the type of doping system used and can include, but is not limited to: dexamethasone or other anti-inflammatory agents, antibiotics, anti-mitotics, growth factors, scar-reducing, poly acrylic acid, dodecylbenzene sulfonic acid (DBSA), p-toluenesulfonic acid (p-TSA) and combinations thereof.

III. Biological Components

The devices, electrodes and coatings for electrode-based devices contemplate the use of one or more biological components. The term "biological component" is a term that can encompass any organic material including a complex material such as an agglomeration of cells such as tissue to the unitary, such as to cellular constituents, for example cell structures such as receptors, ion-channels, membranes, organelles, enzymes, antibodies and chromasomes and polymers of amino acids, sugars and nucleic acids found within, on or produced by cells. In various embodiments, bioactive molecules can be added to the bioelectrode or added to the hydrogel scaffold used to support the growth of cells, tissues and other biological components. Bioactive molecules can be any naturally cell produced protein, lipid, carbohydrate or nucleic acid molecule that can affect any one of the parameters of expression, differentiation or growth of any biological component, but can also include natural and synthetic molecules that can affect the same parameters and can include drugs, pharmaceuticals, biologics and chemicals known to affect such cellular parameters in both prokaryotic and eukaryotic cells. Thus, for the purposes of the present teachings, a biological component can include, but is not limited to: tissue, cells including eukaryotic and prokaryotic cells, archaea, cellular constituents including membranes of cells, synthetic membranes or films mimicking cell membranes with and without membrane proteins including receptors, extracellular matrix molecules, e.g., laminin, collagen and fibronectin, receptors, antibodies, ion-channels, proteins, polypeptides, lipids, carbohydrate containing metabolites enzymes, and nucleic acids (RNA, DNA and cDNA) produced by any cell. In some embodiments, an organic living cell can be any living prokaryotic cell, for example bacterial cells, and eukaryotic cells, for example yeast and mammalian cells found in the various tissues, and organs. Organic living cells can be found in nature or they can be derived from nature and manipulated recombinantly using methods commonly known in the art to introduce exogenous DNA and RNA molecules to alter the expression of proteins and other biomolecules, differentiation and growth characteristics of any cell. In some embodiments, the biological component can be one or more cells derived from electroactive tissue, including without limitation, cardiac cells, neural cells comprising neurons, glial cells and cells that are found naturally in muscle.

In some embodiments, the cells, (eukaryotic or prokaryotic cells such as bacteria can be functionalized by adding functional groups such as RGD, IKVAV, YIGSR peptides, and other functional groups which can be covalently attached to the bacterium, cell or cell part, cell membranes, outer membrane proteins (OMPs), cell surface proteins and the like, or they can be linked to spacers having bifunctional moities that can similarly attach to the bacterium, cell or cell part, cell membranes, outer membrane proteins (OMPs), cell surface proteins and the like. In some embodiments, the eukaryotic cells (including electroactive cells) and bacterial cells can be recombinantly manipulated to express and/or secrete a variety of cellular constituents and bioactive molecules that can be used to enhance the biocompatibility of the bioelectrode, including, growth and differentiation factors, hormones, enzymes, cell surface antigens (CD antigens), and ion-channels that can attract and/or support the cells around the site of implantation.

IV. Biosensors, Diagnostic Devices and Coatings for Devices/Probes and Electrodes In various embodiments of the present teachings, the present conducting polymer structures polymerized in the presence of biological components can be applied onto bare electrode substrates, to enhance preexisting electrode based devices and create enhanced microarray electrode components for sensing, recording and stimulating electrical events in physiological fluid, tissue, cell culture and non-physiologic environments such as those encountered in air sampling and water sampling.

A variety of devices and electrode based systems can be functionally enhanced through the application of the conducting polymer-biological component hybrid material described herein including, without limitation, microelectrode-based neural prosthetic devices, cardiac anti-arrhythmia devices (pacemakers), defibrillators, cochlear, retinal prosthetics, deep brain stimulators and electrode based devices currently used to detect organic and inorganic substrates, drugs, and biologics that rely on the detection of current or changes in impedance, resistance or capacitance or surface energy on the biological component-conductive polymer interface.

The binding of a molecule such as a cognate ligand, drug, substrate to its receptor, ion-channel or enzyme entrapped in conducting polymer can be detected and processed using one or more electrodes and processing components. In some embodiments, enzymes can be embedded in electrochemically polymerized conducting polymer. In various embodiments, enzymes contemplated for the fabrication of biosensors of the present teachings can include any enzyme which participates in a redox reaction when binding to its cognate substrate to any cofactor, including enzyme classes belonging to oxidases, reductases transferases, oxidoreductases, lyases, hydrolases, ligases, and isomerases. Glucose oxidases can be used in the biosensors of the present teachings to monitor glucose. Similarly other medically important enzymes can be used to monitor their cognate substrate in the field of diagnostics lab devices. The bioelectrode can be part of a biosensing device wherein the molecular event of specific binding between the target analyte and the biological component results in a physical change in electrical resistance which can be measured using cyclic voltammetry and impedance spectroscopy. Automated systems are known in the art that can read and transduce the electrical signal obtained from the conducting polymer in response to surface energy and resistance changes occurring at the biological component-conducting polymer and analyte interface to the sensing and processing devices attached to the bioeletrode.

V. Instrumentation and Analytic Tools

The electrodes, electrode based devices and coatings used to modify preexisting electrodes can optionally include controllers, analyzers and other sensing devices and computers that can be used to control the output of electrical current, or voltage. These optional components can also be used to perform, measure and record electrical events, current flow, electrical impedance spectroscopy, cyclic voltammetry, resistance, conductance, capacitance, and potential of the integrated network to the flow of electrons. These analytical systems and devices are commercially available, for example the Brinkman's (Eco Chemie) Autolab system connected to various CPU's (Windows or Macintosh computers) available from Brinkman Instruments Inc., Westbury, N.Y. USA.

VI. Power Sources, Controllers and Analysis

The bioelectrode, electrode based devices and coatings used to modify preexisting electrodes can optionally include power sources, actuators and controllers for the delivery of current and/or voltage for electropolymerization of the conducting monomers around the biological component and for delivery of current and voltage to the conducting polymer in proximate contact with the biological component. Power sources can provide voltage potentials, AC and DC current. In some embodiments, the bioelectrode and electrode based devices employing the biological component-conducting polymer coatings can also be powered with batteries.

B. Methods of Manufacture

I. Living Cell Bioelectrodes and Electrode Coatings

Electrodes can be implemented in any aqueous or liquid-saturated environment, such as in living tissues, in the blood stream, in a lake, river, or ocean, in a complex chemical solution, or in most types of gel. Bioelectrodes can perform a number of activities including 1) direct electrical stimulation or recording of/from a small population of cells, a single cell or a highly localized region of a cell's membrane; 2) extracellular electrical stimulation or recording of cell populations; 3) delivery (passive or temporally controlled) of molecules such as proteins (growth factors), drugs, chemicals, vitamins, toxins, drug-delivering vesicles/particles; 4) sensing/detection of mechanical, electrochemical and/or biochemical information from the environment. Information gained through the recording or sensing features can be relayed to a computer directly through the bioelectrode apparatus or indirectly via other electrodes connected to the sensing devices attached to the recorders and computers. In some embodiments, living cells can be placed in contact with a first electrically conductive substrate such as a metal probe or wire. Biological components, including cells can be grown on the first electrically conductive substrate, alternatively, the first electrically conductive substrate can be inserted or contacted with living tissue or a solution comprising a biological component to produce a biologically interfaced electrode.

As shown in FIG. 1, a solution of monomer for example EDOT 30 is immersed with a biological component which can be any living cell adhered onto an electrode (anode as shown in FIG. 1) The conducting polymer 30 component of the bioelectrode is mixed with an appropriate dopant 34 to provide the necessary redox conditions for polymerization. After an application of galvanostatic or potentiostatic current, the monomers are polymerized with respect to the current emitted from the electrically conductive substrate as shown in FIG. 1 as the anode. Conducting polymer 50 can be deposited directly onto the surface of the conducting substrate/electrode in such a way that any electrical charge transmitted to the electrode is transmitted through the conducting polymer as well, thus the conducting polymer matrix becomes the electrode itself. In some embodiments, the conducting polymer, for example, poly(3,4-ethylendioxythiophene) (PEDOT) can be used to prepare the bioelectrode. Bioelectrodes of the present teachings can have low biodegradability, low electrical impedance, long-term electrical stability under in aqueous solutions, is mechanically soft, can be tailored to have a variety of surface morphologies (varying levels of order, porosity and roughness at the nanometer and/or micrometer scale), and can incorporate natural or synthetic bioactive molecules/proteins (drugs, chemicals, vitamin, growth factors, cell adhesion proteins, signaling proteins, enzymes, substrate for enzymes) in a spatially controlled manor and if desired these molecules can be released in a temporally controlled manor by the application of low electrical currents, and also can incorporate micro or nanoparticles or drug/molecule delivering vesicles.

The biological components, including living cells that in some embodiments can also include electroactive cells such as heart, brain, CNS and muscle cells can be fully integrated into the conducting polymer matrix in such a way that the plasma membranes of the cells are intimately interfaced as shown in FIG. 2 with the polymer molecules allowing for seamless electrical signal transduction between the conducting polymer, the cells, and the electrode. The type(s) of cells incorporated into the bioelectrode device or electrode coatings can be tailored according to the desired function of the resulting bioelectrode. For example, in some embodiments, the use of microalgae can be incorporated as the biological component to conductometrically detect heavy metals and pesticides in an aqueous environment. In other embodiments, the biological component can be growth factor-secreting neural stem cells to be incorporated into the bioelectrode or electrode coatings to promote tissue regeneration and neurite extension toward bioelectrode devices such as a neural prosthetic device implanted in the brain.

II. Cell Templated Electrodes and Electrode Coatings

In various embodiments highly biomimetic electrodes and electrode coatings for preexisting electrode substrates and for microarray electrode based devices having cell features/cell surface features that are templated and patterned with nanometer and micrometer scale surface features are described. The conductive polymers according to the present teachings are capable of being cast into films of varying thicknesses. Monomers of the conductive polymer can be electrochemically polymerized on the electrode. In certain embodiments of the present teachings, conductive monomers are polymerized in the presence of living cells grown on the surface of the electrode. Cells which can be entrapped in the conductive polymer can be electroactive cells, (for example, but not limited to, neurons, skeletal and cardiac cells) capable of conducting electrical signals or cells capable of interacting ionically with the surrounding environment. Target cells in the surrounding environment can chemically react with the embedded cells within the conductive polymer to facilitate signal transduction or other chemical redox (reduction/oxidation) reactions for example ligand-receptor and ligand-enzyme binding events for example as in the glucose oxidase/glucose reaction.

In certain embodiments, the conducting polymer network with cell shaped holes/imprints can be created by electrochemically depositing conducting polymer in the presence of live cells cultured in monolayers on the surface of probe cell-templated electrically conductive substrate followed by removal of the cells. The porous or textured cell-based conductive electrode can encourage cells for example, neurons or myocytes, to intimately interact with the electrode surface due to the high surface area of the fuzzy conductive polymer and the cell shaped imprints. As shown in FIG. 3 panels A-C, the cell-defined polymer topography includes cell shaped holes and imprints as well as micron-sized tunnels, crevasses, and caves in the polymer surface due to for example in the presence of neurons, neurite-templated tunnels of conducting polymer molded around extended neurites that provide invaginations on the neurite length-scale. In certain embodiments, the cell-templated bioelectrodes can be implanted in tissue, resulting in a cell-templated polymer electrode surface that can encourage cells in the host tissue to re-populate the cell shaped holes and send processes into the micron-sized crevasses and caves of the polymer surface. This intimate contact between cells and conductive polymer at one surface and between conductive polymer and an electrode substrate at the other surface will allow for seamless electrical contact between the electrode and the target tissue as shown by the electrical signal benefits provided by cell-templated bioelectrodes coated .

The bioelectrodes having cell-templated features also increase the charge transfer capacity of the electrodes and reduce the electrical impedance experienced by the bioelectrode as compared to a bare electrode wire, due to the increase in effective surface area of the bioelectrode. As shown in FIG. 4, Panel (A) cell-templated PEDOT had an impedance plot somewhere between electrically conductive substrates coated with PEDOT and electrically conductive substrates coated with SY5Y cells embedded in PEDOT (live cell bioelectrodes).

III. Space-Filling Hydrogel Biolectrodes and Electrode Coatings

In certain embodiments according to the present teachings, the biocompatible implantable electrode comprises hydrogel seeded with one or more biological components, for example, living cells through which a conductive polymer network is electrochemically deposited. As shown in FIG. 5, space-filling bioelectrodes can be implanted into living tissue, for example in the brain. The biocompatible hydrogel 120 or three-dimensionally cross-linked macromolecules of hydrophilic polymers can be injected through the skull 90 and can serve as both a nutritive and physically supportive environment for the living cells 110 and as a scaffold for creation of a diffuse conductive polymer network 130 of micrometer and nanometer thin fibers. Once injected into tissue, the cells 110 can be any natural or recombinant cell, for example cells expressing growth factors such as trophic factor to attract neurites to the site of implantation. In certain embodiments, the hydrogel materials can be exceptionally soft, hydrophilic and "tissue-like" thus well-suited for coating of biomedical devices making possible low levels of traumatic injury to host tissue during device implantation. Furthermore, the hydrogel can be supplemented with bioactive molecules, for example, drugs (including, but not limited to anti-virals, anti-microbials, anti-oxidants and anti-inflammatory agents) to inhibit adverse immune system reactions and/or biomolecules (cell adhesion proteins, for example: Integrins, neural-cell adhesion molecule, NCAM; Laminins; Fibronectins; Vitronectins; Cadherins and the like) to promote specific cell-polymer interactions such as synaptogenesis and nerve guidance. The hydrogel matrix can also be seeded with living stem cells which can provide for diverse benefits to the host tissue near the implant site including growth factor secretion to promote local tissue regeneration, recruitment of endogenous stem cells to the device implant site, and a source of multipotent progenitor cells to replace cells that were injured or killed during the device implantation process. The biodegradability of the hydrogel can be controlled to slowly resorb, allowing migrating cells (for example neurons) to penetrate the conducting polymer network, eventually leaving the cells in the host tissue in direct contact with the bioelectrode. Together, the inclusion of additional modulators of inflammation, chemotaxis/adhesion and growth factors can serve at least three distinct functions: (1) the factors can ameliorate and/or mitigate tissue injury and inflammation, (2) increase regeneration at device implant sites, and (3) facilitate intimate contact between the bioelectrode and host cells.

In certain embodiments, living cells can be incorporated into an aqueous hydrogel prior to cross-linking of the hydrogel into a 3D scaffold. According to the methods of the present teachings, many suitable non-toxic hydrogel compositions can be cross-linked in the presence of living cells, including, but not limited to hydrogels comprising calcium (cross-linker) alginate and polyvinyl alcohol (PVA), chitosan, self-assembling peptides and functionalized poly(ethylene glycol)-poly(L-glycolic acid) (PEG-PLGA). The hybrid conducting polymer-cell-hydrogel compositions can be prepared by embedding an electrode in the cell-hydrogel complex for example, but not limited to, by using a conductive substrate such as a platinum, silicon, or gold electrode substrate coated with the cell-seeded hydrogel which can be cross-linked around the electrode, or alternatively, a conductive microwire can be inserted into a cross-linked 3D hydrogel scaffold containing cells within the living tissue to be treated.

For polymerization, the hydrogel-electrode complex can be submerged in an electrically-connected reservoir containing the desired monomer as well as ionic dopants or polyelectrolytes in a saline solution such as PBS or HBSS. Galvanostatic current (typically 0.1-100 $\mu A/mm^2$) can be applied to the electrode substrate and the solution using an AutoLab Potentiostat/Galvanostat (EcoChemie) for 1 minute-2 hours. Electrochemical oxidation/reduction of the monomer results in the formation of a diffuse conducting polymer network within the hydrogel-cell complex. In some embodiments, microfluidic monomer delivery devices can be used to deliver conductive monomer to the cell-hydrogel matrix implanted in the tissue.

As shown in FIGS. 6A and 6B, electrochemical impedance spectroscopy (EIS) and cyclic voltammetry (CV) analysis of space-filling electrodes implanted into living tissue such as the cochlea of a living guinea pig have shown to effectively reduce impedance as shown in Panel (A) as compared to bare gold with in PBS. The space-filling bioelectrodes of the present teachings shows a decrease in impedance over many orders of magnitude relating to the development of a high surface area of conducting polymers in nutritive hydrogel in the guinea-pig cochlea. In Panel (A) and (B) the hydrogel comprised alginate a crosslinking agent and conducting monomer. The conducting monomer was polymerized in situ. The CV shows an increase in charge storage capacity relating to the formation of the conducting polymer network in the porous hydrogel.

In certain embodiments, the hydrogel can be a scaffold or matrix for living stem cells or progenitor cells which can promote tissue regeneration and wound healing at the bioelectrode insertion site. In other embodiments, the hydrogel scaffold can be used as a delivery device for drugs, proteins and other bioactive molecules, and labeling reagents to the target tissues. In certain embodiments, the bioelectrode comprising the conducting polymer network within the hydrogel scaffold can be used to release drugs or other reagents from within the hydrogel or stimulate differentiation of progenitor cells within the hydrogel matrix in a controlled manner. In certain embodiments, the conductive polymer contained within the hydrogel matrix can serve as a mechanically soft and non-immunogenic coating. Furthermore, in certain embodiments, the hydrogel can be used as a "space-filling" electrode that would not necessarily need to be inserted into the target tissue, but rather it could be placed next to the target yet still allow for electrical innervation of the target tissue via the growth of the conductive polymer network contained within the hydrogel.

IV. In Situ Injectable Electrodes

In certain embodiments of the present teachings, the conductive polymer network can be directly polymerized within living tissue thereby reducing the likelihood of electrode damage and tissue damage during and after electrode implantation. In certain embodiments, the resulting conductive polymer network electrode can be in intimate contact with the plasma membrane of living cells. In certain embodiments, the growth of the diffuse biological component-conductive polymer hybrid from the surface of the implanted microfluidic bioelectrode device can create an electrically-connected diffuse network of molecularly thin polymer fibers and chains woven around cells, effectively innervating the tissue. See FIG. 7. In various embodiments, a vessel containing conducting monomer 150 is immersed with the tissue to be implanted with the bioelectrode. In various embodiments, the monomer solution 150 can be injected into tissue 160 for example brain, or heart or muscular tissue. To polymerize the conducting monomer 160 in situ, a working electrode or first electrically conductive substrate 180 is inserted into the tissue where the conducting monomer 150 was injected. Next a second electrically conductive substrate 170 (reference or counter electrode) is place near the first electrically conductive substrate 180 and a constant current is applied to polymerize the conducting polymer in situ. This process can result in the establishment of intimate, specific, and sensitive signal transduction between electrically active cells in the host tissue and the electrode of the implanted device resulting in improved electrical charge transfer capacity of the electrode. See FIG. 7. In certain embodiments of the present teachings, the conducting polymer according to the present teachings can be polymerized within living tissue resulting in fully integrated and efficacious implanted electrodes for example but not limited to: cortical recording/stimulation, deep brain stimulators, peripheral nerve electrodes, cardiac anti-arrythmia treatments (bradycardia, tachycardia and other arythmias), muscle stimulation, surgical ablation (for example epilepsy treatments), pH monitoring, glucose sensing, cochlear implants, and retinal prosthetics. In addition, the diffuse, conductive polymer minimizes the necessity of stiff silicon-based or metal based probe electrodes and signifies a new electrode paradigm built around the super soft nano-electrode integrated with the living tissue. The diffuse conductive polymer networks polymerized off an implanted electrode directly within living tissue can also be independently electrically connected to via additional electrodes inserted within the boundaries of the conducting polymer network. If desired, the implanted electrode from which the conducting polymer network was originally polymerized can be removed and a new, independent electrode can be inserted into the conducting polymer network and can then function as the primary electrode that interfaces with the conducting polymer network.

V. All polymer Electrodes

In some embodiments, the electrode substrate and all of the implanted components are fabricated with polymeric, non-metallic components. The polymer wires/electrodes are non-metallic, non-ceramic, and do not contain metalloids (e.g. Silicon) or alloys. Polymer electrodes are comprised of a conducting polymer or combinations of conducting polymers and non-conductive polymers or hydrogels juxtaposed in specific configurations resulting in an electrode lead that can be used in place of "normal" metal electrodes or wires. In some embodiments, the polymer electrode may also contain carbon or carbon nanotubes. Polymer electrodes can be used in any situation in which it would be unfavorable, dangerous, or impossible to use metal such as in the presence of a magnetic field (e.g. MRI scans of individuals with implanted devices that contain metal electrodes devices or bioprosthetics). Secondly, polymer electrodes can be created several ways from a diversity of substrates and materials and are highly adaptable and can be readily tailored for specific, diverse applications.

C. Methods of Use

The electrodes and electrode based device coatings contemplated in the present teachings offers the ability to improve electrode performance in diverse electronic biomedical device applications including cardiac pacemakers and defibrillators, biosensors, deep brain stimulators, cochlear implants, retinal prosthetics, and drug detection and bioactive delivery devices. In some embodiments of the present teachings, multipurpose conducting polymer coatings that are applied to bare electrodes or preexisting electrode based devices are not only electrically active with low electrical impedance, but they are biocompatible, mechanically soft, and are "fuzzy" with a high surface area at the micro and nano scale thus providing a device surface that facilitates direct interactions and seamless integration between the electrode device and the target tissue or media. Furthermore, these novel electroactive conducting polymers can be made bioactive by incorporating living cells, such as stem cells or cells that have been genetically engineered to express various molecules on their surface, or to produce exogenous bioactive molecules such as growth factors and receptors, receptors, ion-channels, antigens or antibodies, growth factors, or other biomolecules as well as can be tailored to have a variety of surface morphologies including nanofibers and nodules, cell-shaped holes, nanosphere-templates, and neurite-templated microtubes.

The novel functions imparted by the electroactive conducting polymer coatings on implanted biomedical devices described herein correspond to reductions in formation and extent of encapsulation of devices in fibrous scars, improved ability to record high quality electrical signals, increased electrical stimulating capacity, and enhanced device longevity. In some embodiments, the electrode substrates are coated with the electroactive biomaterial of the present teachings comprising an electrically conductive polymer, and a biological component. At least some of the electrically conductive polymer is disposed and polymerized in proximate contact with the biological component and the electrically conductive substrate.

I. Sensing and Recording Electrodes

Chronic implantation of existing microelectrode-based neural prosthetic devices is associated with CNS injury and inflammation which results in neuronal loss around electrode sites and formation of a high impedance glial/immune cell encapsulation of the prosthetic device. Together, these phenomena serve to diminish the quality of recordable neural signals over time following implantation, eventually blocking the capacity to record. This undermines the ability to establish the brain-computer interface that is necessary for function of the cortical prosthetic.

The novel bioactive, biocompatible, low impedance electroactive conducting polymer coatings comprising biological components are an ideal surface modification of recording electrodes on neural prosthetic devices. The "fuzzy", large effective surface area makes for low electrical impedance at the electrode-tissue interface which increases the probability of recording high quality signals from target cells even in the presence of a fibrous glial encapsulation.

In various embodiments, sensing and recording electrodes and microarray electrodes for neuronal activity mapping require fully integrated bioelectrode devices that can interface with the surrounding tissue intimately. Improved electronic responses of these types of electrodes can be achieved by increasing the effective surface area of the electrode. The conductive polymers of the present teachings provide such increase in effective surface area and can support the growth and survival of living cells, for example stem cells expressing growth and differentiation factors in the implanted site. The sensing electrodes can further increase selectivity and sensitivity by mimicking natural scaffolds comprising cells and bioactive molecules including drugs, growth factors, anti-inflammatory agents and antibiotics. In some embodiments, bioelectrodes comprising conductive polymer, polymerized around living cells can be implanted into tissue to enable accurate and higher probability of recording higher quality signals due to the increase in charge capacity and decrease in impedance of the due to immune cell encapsulation and glial scar formation around the bioelectrode. Together, this will allow for more stable and sensitive long-term neural recording than current neural prosthetic electrode technology. Electrodes coated with a cell embedded conducting polymer network of the present teachings can include cortical prosthetics, advanced catheters for electrophysiological mapping of electroactive tissue such as the heart, CNS, brain and muscle.

In some embodiments, electrodes of the present teachings can also be modified to provide highly tissue specific and biocompatible coatings for the attachment of electrically active tissue. Following polymerization of the conducting polymers around one or more biological components and the electrode substrate, the three dimensional surface of the electrode can be made even more attractive to the cells of the surrounding tissue by removing the embedded biological component, for example cells (neurons, myocytes, fibroblasts, stem cells etc) leaving behind cell membrane components and pores or invaginations and three-dimensional structure that facilitates the binding and colonization of adjacent or neighboring cells to the electrode. The resulting electrode is highly integrated and biomimetic, enabling sensitive recordation of functional characteristics of electroactive cells. The inventors of the present teachings have found significant increases in charge transfer capacity and marked lowering of electrical impedance when the electrodes of the present teachings are coated with "fuzzy" cell templated conducting polymer structures. Attracting cells to the electrode and encouraging the neighboring cells to settle and occupy the cell shaped holes, tunnels and crevasses left behind after removal of the biological component from the electrode substrate serves to improve electrode stability, prevent erosion of the electrode surface, diminish electrode biofouling due to adverse immune reactions and improves the performance of the electrode in comparison with hard metal electrodes currently in use.

In some embodiments, cell recruitment and improved communication between the electrode substrate and the surrounding tissue requires more than a cell-templated structure with nanoscale features. For these types or applications, such as implantable electrodes into the brain, heart, and central and peripheral nervous systems, electrode sensing and recording requires an even greater degree of biocompatibility and molecular mimicry. In some embodiments, the electrodes of the present teaching optionally include a hydrogel material that can be implanted into a subject either before insertion of the electrode substrate or can be implanted concomitantly with the electrode substrate in to the subject.

Hydrogel scaffolds comprising alginate, poly-vinyl alcohol and other biocompatible materials can be implanted or injected into the electrode site prior to insertion of an electrode. In some embodiments, the hydrogel scaffold can be biodegradable or non-degradable. For examples of hydrogel scaffolds for use with conducting polymers see Gilmore, K. et al., Polymer Gels and Networks, 2: (1994) 135-143, and Ghosh, S. et al., J. The Electrochem. Soc. 147:1872-1877 (2000). The present teachings provides markedly improved hydrogel scaffolds when in use in situ due to the polymerization of the conductive polymer in the hydrogel in the presence of one or more biological components. In some embodiments, the hydrogel containing the conducting monomer is injected into a site for example a cavity, in interstitial spaces and generally around cells of interest or within tissue then a first electrically conductive substrate is inserted from which a conducting polymer network is polymerized in situ. The conducting polymer network forms around the macromolecules and fibrils that comprise the hydrogel and use these hydrogel components and features as a scaffold for polymerization in a way similar to how the conducting polymer networks form when polymerized directly within tissue. The resultant bioelectrode comprises conductive polymer embedded around cells within a hydrogel framework. In some embodiments, the hydrogel is supplemented with other cells for example, recombinant stem cells producing neurotrophic growth factors, and other biomolecules of interest that can support the growth and development of the surrounding cells and tissue.

In some embodiments, recording devices comprising a biologically integrated bioelectrode device can be used to record or detect electrical signals between cells and between tissues. A method of electrically detecting a transfer of electrical signals between living cells, comprises the steps: providing a bioelectrode device comprising a first electrically conductive substrate in intimate contact with tissue capable of transferring electronic charge. The bioelectrode device includes a first electrically conductive substrate; a biological component; and a conductive polymer electrically coupling the first electrically conductive substrate to the biological component to collectively define a bioelectrode. The bioelectrode transmits or receives an electrical signal between the first electrically conductive substrate any one of the biological component and the conductive polymer. The circuit is achieved by electrically connecting the bioelectrode device and a second electrically conductive substrate electrically coupled with the bioelectrode to a power source. Once connected, the power source is applied providing an effective amount of voltage or current across the first and second electrically conductive substrates, thereby inducing a voltage or current across the conductive polymer. The system detects the transfer of electrical signals with said bioelectrode device.

In some embodiments, the bioelectrode device can also include other electrodes such as a reference electrode, counter electrode and a saturated calomel electrode during sensing, recording, and stimulating cells and for polymerizing conducting monomer.

II. Stimulating Electrodes

Conductive polymer coatings containing one or more biological components such as cells, receptors, cell membranes, cell matrix proteins and the like on electrodes will improve electrical stimulation of cells in contact or in the vicinity of the bioelectrode, including, neurons, myocytes and muscle cells by increasing the charge capacity of electrodes, and by extending conductive surface from a planar electrode towards neurons with fuzzy polymer tendrils. In some embodiments, the bioelectrode and hybrid biological component-conducting polymer electrode coatings of the present disclosure, can also immobilize drugs or living cells to secrete agents for scar prevention/reduction, improve neuronal viability, attract neuronal processes and to promote integration between tissue and the bioelectrode for stable and direct signal transduction. In some embodiments, a bioelectrode comprising a first electrically conductive substrate seeded with neuronal progenitor cells and coated with electrochemically polymerized conducting polymer can be implanted into a neuron rich tissue, such as the brain or central or peripheral nervous system to electrically and biologically stimulate the growth of endogenous neurons. The progenitor neuronal cells can secrete factors that can attract the resident population of neurons to integrate and communicate with the bioelectrode. After integration of the neurons as evidenced by morphological extension of micropodia and neurite outgrowth towards the bioelectrode, the bioelectrode can be actuated by applying a voltage and/or current bias to stimulate the growth of interconnected neurons in communication with the bioelectrode. Without being limited to any particular theory, improved biocompatibility between the bioelectrode and the surrounding tissue can also be attributed to the reduction of inflammation and glial scar formation, facilitation of tissue regeneration near the implanted device, and formation of intimate contact between the electrode surface and target neurons.

In some embodiments, the bioelectrodes of the present teachings can similarly affect the electrical function and well being of other electrically active cells, including cardiac cells or electrically responsive cells such as fibroblasts, and bone forming cells. Hybrid conducting polymer-biological component coatings polymerized on electrode substrates can provide direct integration between electrically-active cardiac muscle cells and implanted electrodes. Electrode coatings comprising fuzzy, soft fibril conducting polymers containing biological components, for example cells or cell membranes, ion-channels, receptors growth factors and enzymes provide increased stimulating charge capacity, while decreasing recording electrode impedance. In some embodiments, cells that are responsive to electrical stimulation such as those involved in wound healing and for therapies related to bone healing and growth can be particularly benefited by stimulation therapies provided by implantable bioelectrodes of the present teachings as a therapeutic form of treatment. Living cells can be grown or otherwise immobilized in natural or synthetic hydrogel scaffolds and fitted with an electrode substrate, for example, a wire or probe before implantation to improve and direct the cellular response to the bioelectrode device and facilitate integration with active tissue. In some embodiments, the living cells embedded in the conducting polymer can include any therapeutically beneficial cell, including cells recombinantly made to express and secrete growth factors, differentiation factors (including one or more of Insulin-Like Growth Factor, NGF family of neurotrophic factors, ciliary neurotrophic factor (CNTF), and pituitary adenylate cyclase-activating peptide (PACAP), Bone Morphogenetic Proteins 1-17, Fibroblast Growth Factor, and any commonly known growth factors used to regenerate neural, cardiac, bone and muscle tissue) receptor agonists and/or antagonists, enzyme inhibitors and other therapeutically effective bioactive agents known to be administered to subjects having diseases and conditions of the electro-active tissue, including the heart, the brain, the central and peripheral nervous system and muscular system.

In various embodiments, tissue regeneration and can be facilitated by implanting bioelectrodes comprising conducting polymers polymerized around embryonic and/or hematopoetic and/or parenchymal stem cells that are capable of differentiating into neurons, muscle cells and cardiac myocytes in a hydrogel scaffold containing anti-inflammatory agents and other growth and differentiation factors. In some embodiments, the bioelectrode can release stored drugs and other bioactive substances, into the tissue-electrode interface, particularly when used as counterions or when added to hydrogel scaffolds. In some embodiments, the nutritive hydrogel scaffold surrounding the bioelectrode can protect the embedded biological component in the conducting polymer and/or hydrogel on or around the bioelectrode from the immune system and provide for their growth and differentiation. Since the hydrogel scaffold containing polymerized conducting polymer is in intimate contact with the electrode substrate through polymerized conducting polymers, electrical therapy may be administered to program the immature electro-active cells for adult cell function.

III. Method of Marking Location of Electrode

In some embodiments, the placement of electrodes including micrometer thin wires and other electrode substrates can make subsequent localization difficult, particularly, if the electrode is devoid of any metallic material or has been removed prior to histological analysis of the tissue. In some embodiments, the bioelectrode, electrode coatings, and in situ polymerized biological component-conducting polymer material described herein can be to modify, preexisting electrodes, can provide a visual cue as to the location or in some cases the former location of the implanted electrode in the tissue. The conducting polymer is typically well contrasted when implanted into living tissue.

IV. Method of Attaching an Electrode to Implanted Tissue

In some embodiments, preexisting electrodes and new electrode devices can be made secure or anchored within the implanted tissue by in situ polymerizing conductive polymer networks within the surrounding tissue from the implanted electrode. This method provides for a "fuzzy" three-dimensional architecture that sends nanoscale fiber, fibrils and other structures into the interstitial spaces of the tissue, thus anchoring the electrode in the implanted tissue. This alleviates the problem of electrode slippage and movement during the period of time the electrode is implanted and can secure the location of the electrode to its proper stimulating or recording site.

V. Organism, Cell, Drug, Chemical, and Biomolecular Sensors

Electroactive conducting polymers can be used to immobilize detecting agents including but not limited to live cells, cell components, nucleic acids, molecule-functionalized micro-nano particles, enzymes, proteins, or peptides on the surface of electrodes without compromising the inherent properties of the conducting polymer which can act as sensing device due to electronic reactions that occur within the polymer when electrical current is applied. This behavior can be exploited to detect oxidation/reduction reactions taking place near the surface of the polymer or within the conducting polymer matrix. Paired with the ability to incorporate a diversity of detecting agents into the conducting polymer matrix, this provides a powerful system for sensing electron transfer reactions that occur between a detecting agent and its complimentary counterpart for example between enzymes and their substrates, receptors and ligands, antibodies and antigens, or cells and pathogens. By sensing the electronic transfer of the immobilized molecules, electroactive conducting polymer electrodes have been shown to detect concentration fluctuations of many molecules including glucose, choline, phosphate ions, nucleic acids, and chlorpromazine and dopamine.

In addition, the conductive polymer can be readily modified to contain a variety of bioactive agents to facilitate interactions with specific proteins or biomolecules and limit non-specific interactions that are associated with device surface biofouling. Proteins can be incorporated into conducting polymer films via a variety of methods such as electrochemical deposition, covalent linkage, and entrapment in the conducting polymer network. This feature of conducting polymers can be exploited to make the conducting polymer network embedded with one or more biological components, bioactive as well as to make possible reversible changes in electrical conductivity triggered by specific stimuli thus allowing the bioelectrode to act as a biomolecule sensing device.

In some embodiments, electrodes comprising conducting polymers polymerized around cells or specific biological components such as receptors, antibodies, ion-channels can be used to detect specific chemical entities. In some embodiments, biological cells, embedded with conducting polymer present on electrode substrates can use the nutrients in the environment to maintain viability while performing a biosensing function by constantly sampling the environment to detect specific (pre-determined by cell type used) biochemical or electrochemical changes. If changes in the environment are detected, the signal is transduced by cell-associated enzymatic reactions which result in local alterations in the net surface charge on the cell or receptor which is then transduced to the electrode via the conducting polymer on the hybrid conducting polymer-biological electrode.

In some embodiments a biosensor can be used to detect a biological material in fluid. The method used to manufacture such a device can include combining and placing a first and second electroconductive substrate on a support. The support can be any biocompatible material that is not subject to degradation such as biocompatible plastics e.g. Teflon, ceramics, e.g. porcelain and metallic materials, e.g. stainless steel. A solution of biological component for example, an enzyme or cell receptor or antibody is applied to a portion of the first electroconductive substrate. The biological component can have a protective, porous and fluid transmissible agent including a biocompatible hydrogel, for example alginate hydrogel to form a layer on the first electrically conductive substrate. Conducting monomer is added to the solution comprising biological component and hydrogel, and are homogenously mixed over a portion of the first electrode substrate. The conductive monomer is then polymerized either by elelctrochemical polymerization by applying a galvanostatic or potentiostatic current to the first electrically conductive substrate or by direct oxidative polymerization, to form a network comprising conducting polymer around the biological component in a hydrogel matrix. A receptacle is prepared (which can include any vessel capable of holding a solution and two electrically conductive substrates, for example a cuboidal flow cell made of non-conductive material), containing a sample comprising a target analyte to be analyzed. In some embodiments, the target analyte can be any substance whose presence or quantity is to be determined. The target analyte is a binding partner to the biological component, for example a specific antigen to its antibody, a specific ligand to its receptor. The first and second electrically conductive substrates are placed in the receptacle. The applied potential is selected to drive an electronic charge transfer including electron transfer between the biological component and the conductive polymer.

Specific binding of the target analyte to biological component results in a measurable potentiometric or amperometric electronic charge difference on the surface of said biological component which is transduced to the conducting polymer which is in intimate contact with the first electrically conductive substrate. The current generated as a result of electronic charge transferred from the biological component to the conductive polymer, then to the first electrically conductive substrate will be directly proportional to the concentration of the target analyte thus allowing for quantification of the concentration of the target analyte. A biasing source applies a constant potential between the first and second electrically conductive substrates when the device is in the receptacle in contact with the fluid containing the target analyte.

In some embodiments, the bioelectrode can contain a thin non-biodegradable hydrogel coating around the hybrid cell-conducting polymer matrix of the bioelectrode to prevent exposure of the biological component with the external environment. Similarly, in still further embodiments, the hybrid cell-conductive polymer electrode can be maintained by providing a source of nutrition to the embedded cells on the electrode. In order to protect the nutritive gel from a potentially toxic environment, an additional thin layer of a non-resorbable hydrogel can be used to protect the nutritive gel from degradation. Providing a source of nutrition to the embedded cells contained and coated with conducting polymer makes it possible for the cells of the bioelectrode to interact (e.g. detect biochemicals or secrete drugs) with the environment without actually being exposed to the environment and without exposing cells/tissues in the environment to the cells of the bioelectrode of the present teachings A novel conducting polymer sensor coating for an electrode-based drug delivery device allowing integration of real-time sensing of the target molecule with feedback to the drug delivery device then stimulation of controlled drug release. A bioactive molecule sensing/monitoring or chemical sampling device that makes possible quantification of even a single target bioactive molecule in a solution. A "smart" polymer surface that can detect when it is in contact with a specific cell type due to an enzyme-mediated sensing reaction that occurs when a ligand within the polymer binds its target receptor. This process could be used to deliver cell-type specific signals from the polymer film.

VI. Bioactive Catheters

To prevent clogging/clotting around implanted catheters, current "smart" catheters use drug-eluting polymer coatings to prevent cell and protein adhesion and encapsulation. The conductive polymer-biological component hybrid polymer coatings of the present teachings can reduce cellular and non-specific protein adsorption through controllable surface charge, controlled reversible shape-transformations, incorporation of bound or releasable drugs or proteins, and by immobilization of living cells which can release therapeutic agents to direct integration of the device with the surrounding tissue.

In some embodiments, the electrode coatings and associated bioelectrode devices that are contemplated by the present embodiments have resulted in the ability to interface conducting polymer with a biological component, for example, plasma membrane of living cells. The present bioelectrode devices can be incorporated as a new type of material for embedding and encasing living cells to facilitate studies on cell surface features due to the ability to form a 3D "negative" image of the cell and on real-time dynamics of the plasma membrane polarization and ion channel activity throughout the cell regions (soma, dendrites/processes). A novel material for immobilizing living cells on a substrate for no or low vacuum microscopic imaging (TEM, AFM, ESEM, EFM) and possibly for other surface analysis techniques that have yet to be used on live cells such as FTIR and SFG.

In some embodiments, the conducting polymer-based microelectrode array (MEA) devices of the present teachings comprising one or more biological components operable to receive an electrical signal and an electrically conductive substrate for receiving the electrical signal; and a conductive polymer matrix comprising a plurality of conductive polymers disposed and polymerized adjacent to the electrode and an biologic component, wherein at least some of the plurality of conductive polymers transmitting the electrical signal between the electrode and the biological component can be used for electrical stimulation and recording of cellular action potentials and extracellular field potentials from single or multiple living electrically active cells. The intimate contact between the conducting polymer and the plasma membrane of cells allows for sensitive, highly localized, even sub-cellular studies on synaptic communication and activation of neural activity which is not possible with currently available MEAs or common patch clamp-based electrophysiologic techniques.

In various embodiments, the bioelectrode can be used in a method for visualization and analysis of cell-substrate adhesions made possible by the inability of the conducting polymer to form on areas of the substrate on which cell membrane is adhered. This reveals the details of the cell-substrate adhesions at the nanometer scale. Use of electroactive biomaterials for these studies would be a cheap, quick alternative to current methods including immunocyto/histochemistry and total internal reflection microscopy (TIRF) which are widely used by the biomedical research community. Quartz crystal microbalance analysis can also be used to assay cell-substrate adhesion but this method is not widely available to biomedical researchers.

The electrode compositions of the present teachings can replace similar biomedical devices implanted in other peripheral tissues of the body.

In certain embodiments of the present teachings, cell-based conductive polymer electrodes are soft, fuzzy materials with low electrical impedance and enormous effective surface areas. The large effective surface area of the conductive polymers can facilitate maximal charge transfer between electrode and target environment. Furthermore, in certain embodiments, the pliability of the conductive polymer can allow for decreased mechanical strain at the interface between the soft tissue and the hard device surface compared to a metal electrode substrate alone.

Furthermore, the bioelectrode can be inserted and implanted in the interstitial spaces in the tissue and in the extracellular matrix between cells resulting in an electrode that can be intimately integrated with cell surfaces yet due to its molecular and nanometer scale, should not trigger an immune response.

The present disclosure will be further understood with reference to the following non-limiting examples.

EXAMPLES

Example 1

Bioelectrodes Comprising Living Cells

Preparation of electrodes and cell cultureware for cell culture: Cells are adhered to or cultured on conductive substrates or electrodes for the electrochemical polymerization process. The electrode is sterilized prior to exposure to cells by washing in 70% ethanol (Sigma-Aldrich, St. Louis, Mo.) for 10 minutes or exposure to UV light for 20 minutes. The sterile electrode is then placed in a dish for culturing the desired type of cells. Depending on the geometry of the electrode in some cases it is necessary to affix the electrode to the bottom of the cell culture dish to reduce lateral movement of the electrode. This is accomplished by gluing the electrode to the bottom of the dish using a minimal volume (e.g. 1-10 ul) of superglue that is adherent in a liquid environment such as Loctite Cyanoacrylate (Henkel Corp., Rocky Hill, Conn.). For most cell types, to allow for cell adhesion, the height of the electrode must be no more than 250-500 um above the surface of the cell culture dish and the electrode surface area should be large enough that a number of cells can be seeded on the conductive surface (e.g. >100 $um^2$). The cell culture dish must have a charged surface to promote cell adhesion, thus we use plasma-treated cultureware from Corning (Corning, N.Y.) and poly(lysine)-coated cultureware (BD Biosciences, San Jose, Calif.). In addition, for some cell types (such as neurons) it is necessary to also coat the electrodes in poly (lysine) to allow for cell adhesion to the surface. To do so, the electrodes are first sterilized then glued to the bottom of plasma-treated cell cultureware then a solution of poly(l-ysine) (1 mg/ml; Sigma-Aldrich) in phosphate buffered saline (PBS; Hyclone Media, Kansas City, Mo.) is added to the dish and allowed to incubate for 2-12 h at room temperature (RT) under sterile conditions (in the tissue culture hood). After incubation, the poly(lysine) solution is rinsed with one wash of PBS, then cells can be plated.

Tissue/cell culture: The cell type of choice is maintained in culture according to published methods appropriate for that cell type. For example, in current studies our laboratory is using the SH-SY5Y neuroblastoma-derived cell line (gift of Dr. Eva Feldman at the University of Michigan; also available at the American Tissue Culture Collection, www.atcc.org) as well as dissociated cortical neuronal cultures from embryonic mice. SY5Y cells are maintained in Dulbecco's Modified-Eagle's Media (DMEM with glucose, with L-glutamine; Gibco/lnvitrogen, Carlsbad, Calif.) supplemented with penn-strep mixed antibiotic solution (dilute 1:100 in cell media; Gibco/lnvitrogen) and 10% fetal bovine serum (FBS; Gibco/lnvitrogen). The media is changed once per week and cells are passaged/split 1:4 every 2 weeks.

Electrochemical polymerization in the presence of the living cells: To generate the living cell bioelectrode, the cell-seeded electrode substrate is placed in an electrically-connected reservoir containing an aqueous solution (depending on cell type) such as water, PBS or HBSS that contains the desired monomer with ionic dopants and/or biomolecules. Galvanostatic current is applied to the electrode and the monomer solution using an AutoLab Potentiostat/Galvanostat (EcoChemie, The Netherlands) or some similar instrument capable of delivering direct current (DC) at 1-10 $\mu A/mm^2$ for 0.5-10 minutes depending on the desired thickness of the conducting polymer film. Electrochemical oxidation/reduction of the monomer results in the formation of conducting polymer films and networks around and onto the adhered cells, thus embedding and immobilizing them in a conductive polymer scaffold. To generate the living cell bioelectrode, the electrochemical polymerization can be optimized for each cell type and electrode configuration so that the resulting hybrid cell-conducting polymer material is such that the polymer surrounds the living cells and their processes but does not cover the entire cell body.

Cell maintenance in the hybrid cell-polymer electrode matrix: In order for the living cell bioelectrode to function properly, the cells incorporated into the hybrid cell-conducting polymer matrix should remain viable for the length of time that the device is expected to function. Living cells require access to a host of nutrients, growth factors, and dissolved gases that are specific to each cell type.

Characterization of surface morphology: The surface morphology of the living cell bioelectrode can not be characterized without destroying the integrity of the "living" electrode 2 batches of electrodes were prepared, 1 batch for electrical characterization and experimentation and another batch for microscopic evaluation. The bioelectrodes are evaluated microscopically to assess cell viability, cell morphology, and integrity/quality of the hybrid cell-conducting polymer matrix using optical and fluorescence microscopy. In addition the surface topography/features are explored using AFM in tapping mode in an aqueous environment and as well as environmental scanning electron microscopy (ESEM) which is performed in a very low vacuum on a chilled stage (Peltier stage) with 50-70% humidity in the chamber.

Optical microscopy is conducted with a Nikon Optiphot POL, having the capability for both reflected and transmitted light observations. Images are acquired with a Spot RT digital camera running on a Macintosh G4 computer. For fluorescent microscopy we use Olympus IMT-2 upright light microscope with Hoffman modulation contrast and a Leica DMIRB fluorescent inverted microscope both with mercury arc lamps for UV light, Olympus CCD cameras, and accompanying Olympus digital imaging software running on Dell PC computers. Information about the sample surface topography will be obtained via AFM with a Digital Instruments Nanoscope IIII with a Multimode head, located in the Michigan Electron Microbeam Analysis Laboratory (EMAL). The images obtained consist of 512×512 arrays of height data over scan sizes typically ranging from 100 microns down to 1 micron. Information about the surface and the microstructure of the living cell bioelectrodes can be obtained using the FEI Quanta 200 3D Focused Ion Beam Workstation and Environmental Scanning Electron Microscope.

Assessment of cell viability: In order for the living cell bioelectrode to function properly, the cells incorporated into the hybrid cell-conducting polymer matrix should maintain viability once embedded in the polymer as well as throughout the lifetime of the device. Cell viability can be assessed using a variety of methods, many of which are cell type specific. Two assays can be used that are common to many types of mammalian cells; the Vybrant Live/Dead Assay (Molecular Probes, Eugene OR) and immunocytochemistry for cell death associated proteins, specifically the apoptosis-associated protease activated caspase 3 (antibody available from Cell Signaling Technologies, Beverly, Mass.). For the Vybrant Live/Dead assay cell quantity, size, and type of nuclear staining intensity are measured using 3 different dyes, specifically Hoechst (permeable to all cells but brighter in nuclei of dying cells), SYTOX green (mostly present in cells dying by apoptosis) and propidium iodide (present in any cell with a compromised membrane; apoptotic or necrotic cells). For immunocytochemistry (ICC), cells are fixed in 3.7% formaldehyde diluted in PBS for 30 min at room temperature (RT) or overnight (ON) at 4 C. Then cells are washed in cold PBS, then permeabilized for 1 h to ON in PBS+0.1% Triton-x (PBSX). Non-specific labeling is blocked by incubating cells for 1 h at RT in 3-5% bovine serum albumin (BSA)+PBSX. Cells are then exposed to the primary antibody (in this case anti-activated caspase 3 @ 1:100) for 2 h-ON diluted in 1.5-3% BSA/PBSX or BSA/PBS. Next cells are washed 3 times in PBS or PBSX, then incubated with the fluorophore-conjugated secondary antibody (1:100 in 1% BSA/PBSX) in the dark at RT. Cells are then washed 3 times in PBSX, all nuclei are counterstained with Hoechst 33342, then cells are mounted in Vectashield aqueous mount and stored at 4° C. until microscopic imaging.

Cultured cells can include, but are not limited to: fibroblasts, neurons, myocytes, smooth muscle, glia, Schwann cells, progenitor cells, embryonic stem cells, neural or other stem cells can be cultured on electrode substrates for the electrochemical polymerization process. The electrode can be sterilized prior to exposure to cells by washing in 70% ethanol (Sigma-Aldrich, St. Louis, Mo.) for 10 minutes or exposure to UV light for 20 minutes. The sterile electrode can be fixed to the bottom of a cell culture dish using a minimal volume (e.g. 1-10 ul) of superglue that is adherent in a liquid environment such as Loctite Cyanoacrylate (Henkel Corp., Rocky Hill, Conn.). To allow for cell adhesion to the electrode substrate, the height of the electrode can be no more than about 250-500 um above the surface of the cell culture dish. The electrode substrate surface area should be large enough that a number of cells can be in contact with the conductive surface (e.g. >20 $um^2$). The cell culture dish surface can be charged to promote cell adhesion, (plasma-treated culture ware from Corning (Corning, N.Y.)) and poly(lysine)-coated cultureware (BD Biosciences, San Jose, Calif.). In addition neurons can be cultured on electrode substrates, after coating the electrode substrate with poly(lysine) to allow for cell adhesion. To do so, the electrodes can be sterilized first then glued to the bottom of plasma-treated cell cultureware then a solution of poly(lysine) (1 mg/ml; Sigma-Aldrich) in phosphate buffered saline (PBS; Hyclone Media, Kansas City, Mo.) is added to the dish and allowed to incubate for 2-12 h at room temperature (RT) under sterile conditions (in the tissue culture hood). After incubation, the poly(lysine) solution is rinsed with one wash of PBS, then cells can be plated.

Tissue/cell culture: The cell type of choice can be maintained in culture according to published methods appropriate for that cell type and as described above. Tissue culture methodologies and materials can be found in Coligan, et al., Current Protocols in Immunology, Wiley lnterscience, 1991 and is hereby incorporated by reference.

Primary neuronal cultures can be prepared from timed pregnant mice (Swiss-Webster) which can be ordered to arrive on embryonic day 13-14. On embryonic day 18,19, or 20, the mouse is sacrificed by $CO_2$ asphixiation, the embryos are removed and immediately placed in ice cold Hank's buffered saline solution (HBSS without MgCI or CaCI; Hyclone Media). The embryos are decapitated and the brain is removed from the skull, the meninges are removed, and the neocortex is dissected. The cortical tissue pieces are placed in 45 ml of ice cold HBSS until dissociation (usually no longer than 20 minutes). The tissue pieces are washed 3 times in fresh ice cold HBSS using a sterile 10 ml pipette to transfer the tissues. Cortical tissues from 10-15 mouse embryos are submerged in 2 ml dissociation media. The dissociation media is composed of Neurobasal media (Gibco/lnvitrogen) supplemented with 0.5 mM L-glutamine (Gibco/lnvitrogen), 5% FBS, and penn-strep (dilute 1:100 in media). A 1000 mL pipette tip is used to mechanically disrupt/dissociate the tissues in the dissociation media (dial pipetter to 500 μl and triturate 20 times, do not generate bubbles). Once the tissues are completely dissociated, the cell suspension is centrifuged at 1000×g for 3 minutes at room temperature (RT). The supernatant is removed and the cell pellet can be resuspended in plating media. Plating media is Neurobasal media supplemented with 0.5 mM glutamine, penn-strep, 1% FBS, 2% B27 serum-free media supplement (Gibco/lnvitrogen). Cells can be plated on poly(lysine) coated cultureware. Every 5-7 days after plating, a 30% media exchange can be performed. Cultures can be ready for experimental use by 7-10 days and can remain useful for as long as 21 days in culture.

Example 2

Cell-Templated Electrodes and Electrode Coatings

Removal of cells to generate cell-templated conducting polymer films: Following electrochemical polymerization on the surface of the electrode substrate as previously described in Example 1, the cells embedded in conducting polymer are removed by mechanical disruption by vigorous shaking in water, saline solutions or exposure to calcium chelating agents (EDTA, EGTA; Sigma-Aldrich) and proteolytic enzymes such as trypsin (Hyclone Media) which cleave proteins that adhere the cells to the electrode substrate. In certain embodiments, the use of water washes and mechanical disruption in combination, will remove the cell bodies and most of the cell material but leaves behind some cell membrane components and cell adhesion proteins normally present on the cell surface. The resulting conducting polymer surface has cell-templated features lined with cell surface and cell-substrate adhesion proteins and/or protein fragments that can facilitate binding of cells and tissues that contact this bioactive and biomimetic material. In contrast, cell removal by exposure to proteolytic enzymes results in a conducting polymer film with cell-templated features but with no inherent biological activity due to the removal of all cell material.

Experimental

Materials and Methods: SH-SY5Y neuroblastoma-derived cells were maintained in Dulbecco's Modified-Eagle's Media (DMEM with glucose, with L-glutamine; Gibco/lnvitrogen, Carlsbad, CA) supplemented with Penn-Strep mixed antibiotic solution (dilute 1:100 in cell media; Gibco/lnvitrogen) and 10% fetal bovine serum (FBS; Gibco/lnvitrogen). Mouse primary dissociated cortical cultures (MCC) were prepared from embryonic day 18-20 (E18-20) mice. The brains were removed and submerged in ice-cold Hanks buffered saline (HBSS; without calcium chloride, magnesium chloride, magnesium sulfate, or phenol red; Invitrogen), the neocortex was dissected, the meninges were removed, tissue was washed in ice-cold HBSS then manually dissociated with a 1 ml pipette tip. MCC were maintained in Neurobasal media supplemented with 0.5 mM L-glutamine and 2% serum-free nutritional supplement B27 (Invitrogen) at 37° C. in 5% $CO_2$. A third of the media was replaced every 4 days, and cells were allowed to mature for at least 7 days before use in experiments.

Electrodes for cell culture: Prior to exposure to cells, electrodes (bare or PEDOT-coated) were sterilized by washing in 70% ethanol (Sigma-Aldrich, St. Louis, Mo.) for 10 minutes. We used two different types of electrodes for these studies, custom-designed, in-house fabricated Au/Pd sputter-coated electrodes (Au/Pd; 6 mm diameter) and Applied BioPhysics (Troy, N.Y.) ECIS electrodes (ABP; 250 μm diameter). For the Au/Pd electrodes, it was necessary to glue the electrode to the bottom of the cell culture dish to prevent lateral movement of the electrode (1-10 ul Loctite Cyanoacrylate; Henkel Corp., Rocky Hill, Conn.). For cell culture, we used plasma-treated polystyrene from Corning (Corning, N.Y.) for all experiments involving SY5Y cells and all experiments involving MCC were performed with poly(lysine) (PDL)-coated cultureware (BD Biosciences, San Jose, Calif.) or dishes and electrodes coated with 1 mg/ml PDL (Sigma-Aldrich) in PBS for 2-12 h (then rinsed in PBS prior to cell exposure). For experiments in which PEDOT was polymerized around the living cells, the neural cells were cultured on the electrode for 24-48 h prior to electrochemical polymerization process.

Electrochemical polymerization and removal of cells from PEDOT: The electrode was placed in an electrically-connected reservoir containing the aqueous monomer solution (for these studies: 0.01 M EDOT and 0.02M poly-anionic dopant poly(sodium styrene sulfonate) (PSS) in phosphate buffered saline (PBS; Hyclone Media, Logan, UT). Galvanostatic current (0.5-10 uA/mm$^2$) was applied to the electrode and the monomer solution using an AutoLab PGstat12 Potentiostat/Galvanostat (EcoChemie, The Netherlands) for 0.5-10 minutes depending on the geometry of the electrode and the desired thickness of the polymer film. For studies on cell-templated PEDOT substrates, cells are cultured on electrodes, PEDOT was electrochemically deposited around the cells, immediately following polymerization the cells were removed by exposure to 100 mM trypsin-versene (Hyclone) at 37° C. for 2 h followed by mechanical disruption.

Microscopy. We used several different types of microscopy to characterize the interactions between electrodes and neural cells. 1) Optical microscopy: Nikon Optiphot POL with a Spot RT digital camera; 2) Phase contrast/fluorescence microscopy: Nikon T2000 inverted light/fluorescence microscope with Hg arc lamp, Hamamatsu CCD 16 bit camera with Simple PCI imaging software (courtesy of Takayama lab); upright Olympus BX-51 with Hg arc lamp, Olympus CCD camera, and Olympus imaging software (University of Michigan Microscopy and Image Analysis Core Laboratory, MIL); 3) Scanning Electron Microscopy (SEM) and Environmental SEM (ESEM): FEI Quanta 3D Dualbeam Focused Ion Beam (University of Michigan Electron Microbeam Analysis Laboratory, EMAL); 4) Atomic Force Microscopy (AFM): Digital Instruments Nanoscope III with a multimode head, tapping mode (EMAL).

Cell Viability Assays: Cell viability was assessed using three assays; the Vybrant Live/Dead Assay (Molecular Probes), the MTT cell viability assay (Chemicon, Temecula, Calif.), and immunocytochemistry (ICC) for the apoptosis associated protease, activated caspase 3 (Cell Signaling Technologies, Beverly, Mass.). For Vybrant Live/Dead assay cell quantity, size, and type of nuclear staining intensity were assessed by fluorescence microscopy using 3 different dyes, Hoechst 33342 (labels all cell nuclei but brighter in nuclei of apoptotic cells), YoPro-3 (labels apoptotic cells) and propidium iodide (PI) (labels cells with compromised membrane; apoptotic & necrotic cells).

Immunocytochemistry and Cell Staining: Cells were fixed in 3.7% formaldehyde/PBS at RT for 30 min-1 h. For ICC, non-specific antibody binding was blocked with 3% BSA/PBS+0.1% Triton X (PBSX), primary antibodies (activated caspase 3; Cell Signaling Technology, Beverly, Mass.) were diluted 1:100 in blocking buffer and incubated with cells overnight at 4° C. The next day cells were washed in PBSX, incubated with secondary antibody (1:300 in blocking buffer), nuclei were counterstained with Hoechst/PBS (Molecular Probes/Invitrogen) then cells were washed, then aqueous mounted with Fluoromount G (Fisher) for imaging. The F-actin cytoskeleton was labeled by Phalloidin-Oregon Green (Molecular Probes) (1:300 in PBSX) for 1 h at RT or overnight at 4° C. For fluorescence microscopy and ESEM, cells were fixed with 4% formaldehyde, maintained in PBS, then washed in water prior to imaging. For SEM cells were fixed using 1% gluteraldehyde, washed in water, then dehydrated in ascending ethanols (50%, 75%, 95%, 100%; 10 min each) then dried overnight in Peldri II or hexamethyidisilazane (HMDS) (Ted Pella, Redding, Calif.).

Electrical Properties Analysis: Electrical testing of electrodes was performed before and after PEDOT deposition using the AutoLab PGstat and a 3 electrode system with PBS (pH 7.0) as the electrolyte, a platinum wire as the counter electrode (CE), a saturated Ag/AgCI calomel electrode (SCE) as the reference electrode (RE). The electrode itself was the stimulating/working electrode (SE/WE). Electrochemical Impedance Spectroscopy (EIS) was used to assess the response to alternating current (AC) over a range of frequencies (1-100,000 Hz), paying close attention to the behavior at 100-1000 Hz, frequencies typically associated with detecting neural activity with microelectrodes. Cyclic Voltammetry (CV) was used to determine the charge capacity of the electrodes. The voltage was cycled from −1 to +1 V or −0.9 to 0.5 V vs. SCE at a rate of (0.1 V/s) while the current was measured.

Equivalent Circuit Modeling: ZSimpWin (EChem Software, Ann Arbor, Mich.) was used to develop a circuit model from the EIS data. Data was imported from the AutoLab PGstat software, Frequency Response Analyzer (FRA). The modeling process was iterative, using the Chi-Square ($X^2$) value for the entire model and the percent error values for each circuit component to determine the fit of a given model to the experimental data. Components were chosen using theories from electrochemical cell studies and using the Boukamp suggestion that each component addition should reduce the $X^2$ value by one order of magnitude. Circuit models are presented using the Boukamp representation. The $X^2$ value was calculated according to the following algorithm:

Experimental Data Point $[\omega_i, a_i, b_i]$

Parameters Associated with $\rho=(\rho_1, \rho_2 \ldots \rho_m)$

Model $[\omega_i, z_i'(\omega_i,\rho), Z_i''(\omega_i, \rho)]$

Calculated Point $[\omega_i, W_i', W_i'']$

Weighing Factors $$\chi^2 = \sum_{i=1}^{n} [W_i'(Z_i'(\omega_i, \rho) - a_i)^2 + W_i''(Z_i''(\omega_i, \rho) - b_i)^2]$$

Chi-Square ($X^2$) Value $W_1'=W_i''=1.0/(a_i^2+b_i^2)$

The $X^2$ value was minimized when the experimental data points correlate with the theoretical data points. This was done by first calculating the difference between the experimental and calculated data points. The difference was squared to give larger variances a greater significance. The differences for all data points were summed and then divided by a weighing factor. A $X^2$ of on the order of $1\times10^{-3}$ or below was acceptable for a given model.

Results and Discussion

In order to study interactions between the conducting polymer, PEDOT and neurons in vitro, we used two different types of neural cell cultures, mouse primary cortical cultures (MCC) and SH-SY5Y neuroblastoma-derived cell line (SY5Y) and two types of electrodes, custom-designed, in-house fabricated Au/Pd sputter-coated (Au/Pd; 6 mm electrode diameter) and Applied BioPhysics (Troy, N.Y., USA) ECIS electrodes (ABP; 250 μm electrode diameter). Cells can be cultured for days to weeks on conducting polymers such as PEDOT and poly(pyrrole) with little or no toxicity. However effects of the monomer on cell viability were not known. Therefore we first determined the cytotoxicity dose-response curve for serial dilutions of the PEDOT monomer, ethylenedioxythiophene (EDOT) and the poly-anionic dopant poly (styrene sulfonate) (PSS, 0.02M). We found that both SY5Y cells and MCC could be exposed to as much as 0.01 M EDOT, 0.02M PSS for as long as 72 h while maintaining at least 75% cell viability. Therefore since we typically used PEDOT polymerization procedures of 30 sec-10 min. in duration, we expected cytotoxicity would be negligible.

Polymerization of PEDOT around living cells. To investigate whether PEDOT could be polymerized directly in the presence of live neural cells, we electrochemically deposited PEDOT using 0.5-1 uA/mm$^2$ galvanostatic current from a monomer solution containing 0.01 M EDOT, 0.02 M PSS in PBS onto electrodes seeded with neural cells. This resulted in formation of PEDOT on the electrode, surrounding and embedding the cells. We assessed the morphology and topology of the PEDOT polymerized around the neural cells using optical microscopy and scanning electron microscopy (SEM). After deposition, PEDOT appeared as a dark, opaque substance around the cells and the cells and their nuclei remained intact throughout and following polymerization. Interestingly, PEDOT deposition was prohibited in areas where cells were evidently strongly adhered to the substrate. Using SEM, we found that the PEDOT on the electrode and around the cells displays the fuzzy, nodular surface topology that is typical of PEDOT. The polymer also appeared to wrap around the exterior of the cells and their extensions, in some cases growing over, engulfing the cell body.

Generation of cell-templated PEDOT coatings. We next adapted these techniques to generate conductive polymer substrates with biomimetic topology consisting of cell-shaped holes and imprints on the same scale as cell surface features. Following polymerization of PEDOT around the neurons, the cells and cell material was removed from the PEDOT matrix using enzymatic and mechanical disruption. This resulted in a neural cell-templated, fuzzy PEDOT material with a combination of nanometer and micrometer scale features. The neural cell-templated polymer topography included neuron-shaped holes and tunnels, crevasses, and caves resulting from conductive polymer molded around cell bodies and extended neurites. Using this method, we found evidence of intimate contact at the interface between the PEDOT matrix and plasma membrane of the cells in which the PEDOT (dark substance) revealed nanometer scale tendrils at the leading edge of a neurite. AFM images provided further details about the topology of the polymer surface, indicating that the neuron-templated features were about 1.5-3 μm in height.

We hypothesized that the biomimetic surface of the cell-templated PEDOT would be attractive to cells due to its nanometer scale "fuzziness" and the unique cell-shaped holes and imprints. After new cells were seeded on top of the cell-templated PEDOT, we probed for evidence of cell repopulation of the cell-shaped holes or of increased adhesion to the cell-templated surface. We found that SY5Y cells cultured on the neuron-templated PEDOT substrate showed a preference for adhering to the cell templated zones over the regions of un-templated PEDOT. A subset of cells did seem to re-populate the cell-shaped holes of the film, however these cells did not settle down into the exact position as the original cells used for templating.

Assessment of cellular responses to embedding in PEDOT. To better understand cellular responses to the electrochemical polymerization procedure and embedding within the PEDOT matrix, we assessed cell viability, morphology of the cytoskeleton and nuclei, cell adhesion, and cell membrane integrity during minutes to days after polymerization. For these experiments, we used polymerization procedures which resulted in PEDOT matrices that did not completely engulf the cells so that cellular activity and access to nutrients could be retained. We found that the cells did not undergo lytic or necrotic death as evidenced by normal nuclear morphology (Hoechst 33342 staining) after the first 24 h following polymerization. Therefore we assayed the cells for programmed cell death or apoptosis which can occur 24-96 h following the triggering insult using the Vybrant Live/Dead assay (Invitrogen) and immunocytochemistry for activated caspase 3 (Cell Signaling Technologies), an apoptosis-associated protease. Indeed, starting at 72 h following polymerization we began to detect increasing percentages of apoptosis in cells embedded in the PEDOT matrix as indicated by the presence of activated caspase 3 in the nuclei. For example, comparison of percentages of activated caspase 3 (+) cells in MCC at Oh (FIG. 5*c*) and 120 h post polymerization. Apoptotic cell counts at 0 h after polymerization revealed few if any apoptotic cells however by 120 h after polymerization, 25% and 33% apoptotic cells were detected in SY5Y and MCC, respectively.

Cells were stained with propidium iodide (PI), a nucleic acid dye that is impermeable to cells with intact plasma membranes. The PI (+) staining was transient and by 24 h there was no significant difference between electrochemically polymerized cells and controls (no current exposure). The cells were surrounded by a thick, dense PEDOT matrix (dark, opaque substance) that covered most of the neurites leaving exposed only the tallest cell regions near the soma.

Characterization of the electrical properties of PEDOT containing cells. We next characterized the electrical properties of the neuron-templated PEDOT and PEDOT+live neuron electrode coatings using Electrical Impedance Spectroscopy (EIS) and Cyclic Voltammetry (CV). Recording of electrophysiological signals from electrically active cells such as neurons and cardiac myocytes are typically performed at frequency ranges from 0.1-1 kHz with low impedance, sensitive electrodes which provide the highest signal to noise ratio and number of recordable units. Electrode impedance is related to interfacial surface area between the electrode and electrolyte with impedance decreasing as surface area increases. Consistent with previous reports, coating of electrodes with PEDOT results in lowering of electrode impedance 1-2 orders of magnitude across frequencies between 0.01-100 Hz. This is evidently due at least in large part to an increase in effective surface area of the electrode which is provided by the fuzzy, nano-porous yet conductive PEDOT matrix. Compared to PEDOT alone, the impedance of the PEDOT+neurons coating is increased due to the presence of the cells. This is likely associated with decreased PEDOT coverage of the electrode surface because the cells act as a barrier to PEDOT polymerization on some regions of the electrode. However our unexpected finding that neural cell-templated PEDOT coatings showed impedance spectra between that of electrodes coated with PEDOT and PEDOT+neural cells suggests that some of the increased impedance of PEDOT+neurons compared to PEDOT could be due to the electrically-active nature of the cells which may interfere with signal transduction between the electrode and the PEDOT. Compare the 1000 Hz impedance (Z) of the bare, uncoated electrode (4.4 kOhms) to that of an electrode seeded with neural cells (2.7 kOhms), the PEDOT-coated electrode (0.2 kOhms), the PEDOT+live neural cells electrode (1.3 kOhms), and the neural cell-templated PEDOT electrode (0.7 kOhms).

The phase plot of the impedance spectroscopy reveals phase angles of 75-85° for the bare and neural cell-seeded ABP electrodes at frequencies of <10 kHz indicating that the electrode is primarily functioning as a capacitor. Coating with PEDOT dramatically drops the phase angle to <20° making the electrode more resistive as opposed to capacitive at frequencies above 0.1 kHz. However the presence of neural cells within the PEDOT matrix tempers this response attenuating the decrease in phase angle so that it does not become primarily resistive until >10 kHz frequencies. This is likely due to complex interactions between the neural cell membranes which inherently have both resistive and capacitive components (usually represented by RC circuit with depolarization resistance R and membrane charge storage capacity C and the unique microstructure of the PEDOT matrix that forms when PEDOT is polymerized in the presence of live cells.

To better understand how the PEDOT+neuron and neuron-templated PEDOT coatings related to PEDOT coatings in terms of their ability to decrease the electrical impedance of an electrode, we compared them to two similar PEDOT coatings that we characterized in previous publications. PEDOT+neuron and neuron-templated PEDOT coatings were compared to a PEDOT coating comprising of an EDOT monomer solution containing the same poly-anionic dopant, PSS used in the present studies as well as a PEDOT coating templated with 485 nm poly(styrene) spheres using a method similar to the methods presented here for preparing cell-templated PEDOT. Because we have used a variety of electrode types and geometries in our publications, for comparison purposes the data were normalized for electrode surface area ($Z*A=Ohms*m^2$) and the 1 kHz impedance values were graphed as a function of deposition charge density ($C/A=C/m^2$).

We have also performed equivalent circuit modeling to better understand how increasing complexity, microporosity, and non-uniformity of PEDOT coatings can dramatically affect resistivity of the PEDOT coatings. A typical bare electrode can be represented by $RS(T(R_TQ))$ where $R_s$ is solution resistance, T is a diffusion-related finite Warburg element (constant phase element $Q_n$=0.5), $R_T$ is charge transfer resistance at the electrode-electrolyte interface, and Q is a constant phase element representing the porosity and interfacial capacitance of the electrolyte-electrode interface. Previously, equivalent circuit models for PEDOT-coated electrodes have been defined as $R(C(R_TQ_n=0.5))$ in which the T of the bare electrode is substituted for a C (capacitor) due to the diffusion of ions at the polymer surface and current conduction through the polymer that is more capacitative than for the bare electrode. Interestingly, modeling calculations for PEDOT, PEDOT+neurons, and neuron-templated PEDOT coatings on ABP electrodes indicated that the PEDOT matrix was best represented by a constant phase element $Q_n$=0.97 for PEDOT alone, $Q_n$=0.88 for PEDOT+neurons, and $Q_n$=0.72 for neuron-templated PEDOT (see Table 2). This decreasing trend represents an increase in the surface porosity of the PEDOT which can be corroborated by qualitative analysis of PEDOT, PEDOT+neurons, and neuron-templated PEDOT which indicates that neuron-templated PEDOT has the highest gross porosity due to the presence of cell-shaped holes in the PEDOT matrix.

The presence of neural cells in the PEDOT matrix contributed an RC element typical of neural cell membranes that was in parallel with the C(RQ) of the PEDOT resulting in $[R_s(C(R_TQ)(RC))]$. Interestingly the same model could be applied to neural cell-templated PEDOT yet in this case the additional RC was contributed by the capacitative gaps left behind after removal of cells from the PEDOT matrix rather than by the effects of the cell membranes. Despite having the same model, the values for both the resistor and the capacitor in the RC element are higher for the PEDOT+neuron coating ($R=3.18\times10^{-3}$ Ohms cm$^2$, $C=2.46\times10^{-1}$ F/cm$^2$) as compared to the neuron-templated PEDOT coating ($R=7.14*10^{-3}$ Ohms cm$^2$, $C=7.66\times10^{-1}$ F/cm$^2$). This increase in resistivity and capacitance manifested in an increase in charge transfer capacity that can explain why neuron-templated PEDOT is more conductive than the PEDOT+live neuron matrix.

Cyclic voltammetry was used to assess the charge transfer capacity of the PEDOT, PEDOT+neurons, and neuron-templated PEDOT coatings on Au/Pd electrodes. The dramatic increase in charge capacity (area under CV curve) for PEDOT and neuron-templated PEDOT-coated electrodes as compared to the bare Au/P electrode is consistent with PEDOT coatings. CV spectra show the intrinsic redox reaction of the electrode material as the potential of the electrode bias is cycled from negative to positive and back. This propels ion exchange between the electrode and the electrolyte moving mobile charge carriers in and out of the PEDOT matrix. This voltage bias switching process can be repeatedly applied to PEDOT-coatings with little or no degradation of the electrical or physical stability of the film, making PEDOT-coated electrodes ideal candidates for biosensing and drug-releasing biomaterials applications. The charge capacity for the PEDOT+neuron electrode coating is also greatly increased over the bare Au/Pd electrode seeded with neural cells but does not reach the level of that seen for PEDOT and has a distinctly different shape.

Interactions between neural cell cultures and the conducting polymer PEDOT are advantageous for the development of electrically conductive biomaterials intended for contact with electrically-active tissues such as the brain and heart. PEDOT was electrochemically polymerized directly in the presence of neural cells seeded on electrodes resulting in the formation of a conducting polymer matrix around and onto adhered cells. SEM and optical imaging suggested that polymerization from a monomer solution enabled the polymer to deposit at the cell-electrode interface, apparently using the cells, cell membranes, and extracellular matrix (ECM) as scaffolds for polymerization.

Electrical characterization of the PEDOT matrix containing live neural cells suggested a relationship between the electrode and neural cells that is distinct from a more typical configuration used for electrically interfacing neurons in which neural cells are cultured on or near metal electrodes. Intimate interactions between the conducting polymer and the neuronal membrane were revealed as PEDOT covered delicate filopodia and neurites. This unique cell-polymer-electrode interface can be an ideal candidate material for the development of a new generation of biosensors and "smart" bioelectrodes. The incorporation of electrically-responsive, electrode-adherent cells into a conducting polymer matrix provides for an additional opportunity to exploit both the biochemical and electrochemical qualities of the incorporated cells for sensing purposes.

PEDOT polymerized around cells cultured on electrodes also indicated that the process of electropolymerization around living cells is a novel method for capturing and immobilizing cells in a fixed, conductive matrix. Trapping cells on an electrode site in PEDOT can simplify multi-electrode array (MEA)-based electrophysiological studies of signaling in neural networks which is currently made difficult by migration of neurons off electrode sites. Electropolymerization of cells on an electrode can facilitate imaging of cells using Atomic Force Microscopy (AFM) and Scanning Tunneling Microscopy (STM) which require conductive substrates and/or immobilized targets. We also noted that PEDOT polymerized around cells cultured on electrodes is a novel method for revealing a "negative" image of the morphology of the cell-substrate adhesions due to the manner in which PEDOT is deposited around the exterior of the cells. This can provide an alternative to other methods for visualizing cell-substrate interactions such as immunocytochemistry and Total Internal Reflection Fluorescence (TIRF) microscopy.

We next generated neuron-templated PEDOT coatings by removing the cells and cell material from the PEDOT matrix after polymerization around the cells. We hypothesized that a cell-templated surface would be cytomimetic, probably biocompatible and possibly cell-attractive. Indeed the cell-defined PEDOT matrix provided surface features on the cell and neurite length-scale and included tunnels, troughs, crevasses, and caves resulting from PEDOT molded around extended neurites and various cellular processes. Our in vitro findings presented herein indicates that when implanted in tissue, this cell-templated polymer surface can encourage cells in the host tissue to re-populate the cell-shaped holes and send processes into the tunnels and crevasses. This would provide for very intimate contact between cells and the conductive polymer making possible continuous electrical contact between the electrode and the tissue. Variation in cell removal techniques can provide an opportunity for spatially-localized biochemical control of interactions between target cells and the electrode at the cellular and subcellular length-scale. When coupled with the mechanical control provided by the cytomimetic topology, tailoring of the biochemistry of the cell-templated surface could make possible precise manipulation and tracking of neurite guidance, growth, and signal transduction.

Consistent with other conducting polymer electrode coatings, the cell-templated PEDOT and PEDOT+neuron coatings described herein demonstrates the ability to enhance electrode functionality as indicated by decreased electrical impedance of at least 1 order of magnitude at 1 kHz and charge capacity increases of 2-4× the bare electrode. Hence, paired with their biomimetic properties, these novel electrode coatings are excellent candidate materials for improving the electrode-tissue interface.

Example 3

Bioelectrodes Comprising Cells Contained Within a Hydrogel Scaffold

The bioelectrode comprises living, active cells, immobilized in a 3D hydrogel scaffold with conductive polymer networks deposited through the gel and around cells. The conductive polymer allows the bioelectrode to relay electric or electronic signals to and from other devices for electrical communication. The cells suspended within the hydrogel can be monitored directly with the electrode, and can also be used to biochemically or electrically interact with the desired communication source.

Methods and Materials: Tissue/cell culture: Cells are harvested as described in Example 1. For neuronal cells as prepared according to Example 1, are plated on poly(lysine) coated cultureware. Glial cells in the culture can be limited by not including FBS in the media used for media changes. Cells are grown according to Example 1. Prior to immobilization in the hydrogel scaffold, cells cultured in dishes are enzymatically removed from the substrate by incubation with Trypsin-EDTA 0.25% (Gibco/lnvitrogen) at 37° C. for 10-15 minutes. The cells and media are the centrifuged at 1000 RPM for 2 minutes and the supernatant is discarded. The remaining cell pellet is resuspended and triturated to dissociate cells in enough media for a concentration of $10^5$-$10^7$ cells/ml.

In certain embodiments, alginate and poly(vinyl alcohol) (PVA) hydrogels can be used however, the method can be adapted to a number of biocompatible hydrogels or chemically-functionalized hydrogels with non-toxic crosslinking. Alginate hydrogels are made from high G, medium viscosity alginate powder (Sigma Aldrich, St. Louis, Mo.) dissolved in PBS (1-6% (w/v)) and then filter sterilized using 0.45μm syringe filters (Fisher Scientific, Hampton, N.H.). The alginate:PBS solution is then thoroughly mixed with enough of the cell solution for a cellular concentration of $5\times10^4$-$5\times10^6$ cells/ml and an alginate concentration of 0.5-3% (w/v). Crosslinking is achieved by addition of a sterilized source of divalent ions, such as $Ca^{2+}$ or $Mg^{2+}$. Thin (5μm-2 mm) electrode coatings of hydrogel containing living cells are applied by dipping electrodes or wires into the hydrogel-cell solution and then by submerging the electrode in a 2% (w/v) $CaCI_2$ (Sigma-Aldrich) solution in deionized water which has been sterilized using a 0.22 μm syringe filter (Fisher Scientific). Repeated hydrogel applications and crosslinkings can be used to create thicker coatings. Larger (up to 10 $cm^3$) bulk hydrogels are made by thoroughly mixing the hydrogel-cell aqueous solution with a filter sterilized 4% (w/v) $CaSO_4$ solution in deionized water in a molar ratio of 0.18. The gel is then injected into a sterilized mold or receptacle of choice. Hydrogel scaffolds can be temporarily stored in PBS or HBSS during fabrication of the hydrogel-space filling bioelectrode.

Electrochemical polymerization in the presence of the living cells: The cell-seeded hydrogel-coated electrode can be placed in an electrically-connected reservoir containing a saline solution such as PBS or HBSS that contains the desired monomer with dopants and/or biomolecules. For bulk hydrogels, an electrode or microwire is inserted into the hydrogel. Galvanostatic current is applied to the electrode and the monomer solution using an AutoLab Potentiostat/Galvanostat (EcoChemie, The Netherlands) or some similar instrument capable of delivering direct current (DC) at 1-10 $\mu A/mm^2$ for 0.5-120 minutes depending on the desired thickness of the polymer film. Electrochemical oxidation/reduction of the monomer results in the formation of conducting polymer films and networks through the hydrogel network and around the cells, thus embedding and immobilizing them in a 3D conductive polymer hydrogel scaffold.

Assessment of cell viability: Viability of cells in contact with the conductive polymer electrode networks can only be assessed as described in Examples 1 and 2.

Characterization/measurement of functionality & effectiveness: Characterization of surface morphology: Assessment of the electrical properties: The combination of the micrometer and nanometer scale surface roughness of the conducting polymer film/network and the cell-templated pores and tubes that result from electrochemically polymerizing in the presence of the living cells can manifest in an increase in effective surface area of the electrode and thus significantly decreases the electrical impedance while increasing the charge capacity of the electrode. To assess these changes, we measure the electrical properties of the 3-dimensional electrode network by performing Electrical Impedance Spectroscopy (EIS) and Cyclic Voltammetry (CV). We use the Brinkmann Autolab system connected to a Dell computer to perform these measurements. A solution of 0.1 M PBS (pH 7.0) is used as the electrolyte in a three-electrode cell. A platinum foil is used as the counter electrode and a saturated calomel electrode is used as the reference electrode. The conductive polymer electrode network is connected to (and becomes) the working electrode.

For EIS, an AC sinusoidal signal of 5 mV amplitude is used and the DC potential set to 0. The values of the impedance are determined at five discrete frequencies per decade over the range of $10^5$-10 Hz. The real and imaginary components of the impedance are measured as a function of frequency and plotted in various format (amplitude vs. frequency, phase angle vs. frequency, real part vs. imaginary part) for analysis. For CV, the three-electrode cell setup is the same as the one used for EIS. A scan rate of 10 mV/s will be used and the potential on the working electrode will be swept between-1.0 to 1.0 V vs. SCE. This limit is wide enough to include the reversible redox reaction and narrow enough to avoid over-oxidation and remain in the water window.

Example 4

In situ Polymerized Electrode Networks

In this embodiment, the conductive polymer is a diffuse network of molecularly-thin and nanometer scale conductive polymer fibrils that is grown in situ through interstitial spaces in tissues and within the extracellular matrix between cells. To fabricate the bioelectrode within a tissue, it can be necessary to have an electrode substrate on an implantable biomedical device from which the polymerization of the conducting monomer is achieved by the delivery of electrical current through the electrode site. For polymerization of the conductive polymer, the tissue near the electrode site must be saturated in the non-toxic monomer solution which can be accomplished by delivering monomer via microfluidic channels in the biomedical device or by injection.

When electrical current is delivered in the presence of the monomer solution, the polymer electrode first deposits on the electrode site itself and then grows off the electrode site, following the electric field generated by the electrode. The result is creation of an electrically-connected diffuse network of thin polymer fibers and chains woven around and between cells, effectively innervating the tissue and intimately contacting the plasma membranes of cells in the 3D space of the living tissue. The diffuse polymer network electrode is fully integrated within the living tissue and it maintains electrical integrity and stability as it moves with the tissues, eliminating micromotion-associated tissue damage that is often seen with physically tethered or stiffer electrodes that are not well-integrated at the tissue-device interface.

In certain embodiments, the conductive polymers can be polymerized within a variety of tissues including, but not limited to, epithelial tissue, dermis, cardiac muscle, and brain. Due to its ability to grow within & through nanometer thin spaces between cells for lengths of at least 500 um to 1 mm from the electrode site, this type of 3-dimensional electrode network can penetrate and bypass fibrous scar encapsulations and congregations of immune cells that often form around implanted electrodes. This makes possible the establishment of functional long-term electrical communication between implanted biomedical devices and the healthy target cells tissue despite encapsulation of the device in high electrical impedance and the presence of signal blocking scar tissue.

Synthesis of Diffuse Polymer Electrode Networks: An electrode or a biomedical device with 1 or more electrode sites is inserted into the target tissue. The electrode must be electrically connected (through electrical wires or some sort of telemetry) to an instrument and/or computer that can deliver electrical stimulation to the electrodes of the implanted device. For polymerization of the conductive polymer, the tissue near the electrode site must be saturated in the non-toxic monomer solution which can be accomplished by delivering monomer via microfluidic channels of the biomedical device or separately by injection or infusion.

Polymerization in tissue for acute in vitro testing: The tissue (e.g. brain, heart, skin, muscle, etc.) in which the Diffuse Polymer Electrode Network is to be polymerized is dissected from an euthanized ($CO_2$ overdose) adult Swiss-Webster mouse and immediately submerged in ice cold monomer solution for 10-30 minutes at 4° C. The monomer solution is a saline (PBS or HBSS) solution containing 0.01M 3,4 ethylene dioxythiophene (EDOT), 0.25 mg/ml of the ionic dopant poly(styrene sulfonate) (PSS). A variety of other dopants and biomolecules can also be included in the monomer solution. After incubation in the monomer solution, the tissue can be placed in an electrically-connected reservoir filled with chilled monomer solution and a 75 um diameter gold (Au; Teflon-coated) microwire (Ted Pella, Redding, Calif.) electrode is inserted into the desired position in the tissue. Galvanostatic current is then applied to the electrode and the monomer solution using an AutoLab Potentiostat/Galvanostat (EcoChemie, The Netherlands) or some similar instrument capable of delivering direct current (DC) at 1-10 $\mu A/mm^2$ that is connected to a computer and electrical analysis software. The polymerization procedure is run for 15 min-4 h at room temperature (RT). Electrochemical oxidation/reduction of the monomer results in the formation molecularly-thin and nanometer scale conducting polymer tendrils and networks around the cells in the tissue within the interstitial spaces. After the polymerization procedure, the tissue (with implanted electrode) can be fixed by submersion in either 4% paraformaldehyde or 2.5% glutaraldehyde (both diluted in PBS) overnight (ON) at 4° C. The next day the tissue is washed in PBS then prepared for tissue sectioning.

Polymerization in organotypic brain slice cultures for chronic testing: Male rats or mice (5-10 days old) are deeply anesthetized by isofluorane exposure then rapidly decapitated. The brain is removed and placed in an ice-cold dissection medium consisting of Hanks buffer with 25 mM HEPES and 6% glucose. The hippocampus and neocortex are dissected out and sliced transversly at 400 um thickness. Slices are placed on planar microelectrode arrays (MEAs from MultiChannel Systems Reutlingen, Germany) in 35 mm poly (lysine)-coated tissue culture dishes (BD Biosciences, San Jose, Calif.) or a 75 um diameter gold (Au, Teflon-coated) microwire (Ted Pella) is inserted into the slice and the slice is placed on a semi-porous membrane (0.4 um, Millipore, Billerica, Mass.). Slices with electrodes are cultured in growth media containing 50% MEM, 25% horse serum, 25% Hanks buffer, 20 mM HEPES, 1 mM glutamine, and 5 mg/ml glucose at 5% CO2 at 37° C. Cultures are maintained for 3-21 days in vitro with media changes every 2-3 days prior to or during use in experiments. 3-7 days after culturing, the tissues are submerged in media containing monomer (0.01M EDOT) and allowed to incubate for 1-4 h at 37° C. Next the electrode in contact with the tissue slice is electrically connected to an AutoLab Potentiostat/Galvanostat (EcoChemie, The Netherlands) or some similar instrument capable of delivering direct current (DC) at 1-10 $\mu A/mm^2$ that is connected to a computer and electrical analysis software. Galvanostatic current is then applied to the electrode in the tissue for 15 min-1 h under in vivo conditions (5% CO2 at 37° C.) to maintain cell viability. Electrochemical oxidation/reduction of the monomer results in the formation molecularly-thin and nanometer scale conducting polymer tendrils and networks around the cells in the tissue within the interstitial spaces. After the polymerization procedure the tissue is placed back in the incubator for a chosen time course following polymerization then at the end of the experiment, the tissue (and associated electrode) is fixed by submersion in either 4% paraformaldehyde or 2.5% glutaraldehyde (both diluted in PBS) overnight (ON) at 4° C. The next day the tissue is washed in PBS then prepared for tissue sectioning.

Diffuse Polymer Electrode Network characterization/measurement of functionality & effectiveness: Characterization of Diffuse Polymer Electrode morphology: Diffuse Polymer Electrodes can be synthesized dynamically, in real-time from an electrode implanted in living tissue. Diffuse polymer electrode networks are another example of a 3-dimensional polymer electrode network. Tissues containing the diffuse polymer electrode are usually too thick for imaging by available microscopy methods, the tissue must be sectioned. This can be accomplished in one of several ways depending on the type of tissue staining and microscopy to be performed: 1) fixed or un-fixed tissue is wrapped in aluminum foil then flash frozen in liquid nitrogen or dry-ice cooled isopropanol then embedded in Tissue-Tek O.C.T Compound (Electron Microscopy Sciences, Hatfield, Pa.) and microsectioned (4-20 um slices) by Cryostat; 2) fixed tissue is dehydrated, xylene processed, embedded in paraffin, then microsectioned (4-12 um slices) by microtome; 3) un-fixed tissue is embedded in 10% gelatin (<50° C.) then sectioned (20-500 um) by vibratome; 4) fixed tissue is embedded in 10% gelatin, the tissue+gelatin complex is fixed ON at 4° C., then sectioned (20-500 um) by a vibratome.

Once sectioned, the diffuse polymer electrode networks are evaluated microscopically to assess cell viability, cell morphology, and integrity/quality of the fully integrated hybrid tissue-conducting polymer network using optical and fluorescence microscopy. In addition the surface topography/features are explored using AFM in tapping mode in an aqueous environment and as well as environmental scanning electron microscopy (ESEM) which is performed in a very low vacuum on a chilled stage (Peltier stage) with 50-70% humidity in the chamber. Optical microscopy is conducted with a Nikon Optiphot POL, having the capability for both reflected and transmitted light observations. Images are acquired with a Spot RT digital camera running on a computer.

For fluorescent microscopy we use Olympus IMT-2 upright light microscope with Hoffman modulation contrast and a Leica DMIRB fluorescent inverted microscope both with mercury arc lamps for UV light, Olympus CCD cameras, and accompanying Olympus digital imaging software running on Dell PC computers. In addition for thick tissue sections (>20 um) we use a Zeiss LSM 510 confocal microscope mounted on a Zeiss Axiovert 100M inverted microscope with UV, Argon, and 2 green HeNe lasers that deliver up to four images with transmitted light images and the accompanying Zeis META digital image analysis software that is run on a Dell PC. Information about the surface and the microstructure of the in situ polymerized bioelectrodes will be obtained using the FEI Quanta 200 3D Focused Ion Beam Workstation and Environmental Scanning Electron Microscope and a Philips CM-100 transmission electron microscope (TEM) equipped with an automated compustage and Kodak 1.6 Megaplus high resolution digital camera.

Assessment of the diffuse polymer electrode network electrical properties: The network of molecularly-thin and nanometer scale conducting polymer fibrils that results from electrochemically polymerizing on the scaffold of the living tissue manifests in a large increase in effective surface area of the electrode and thus significantly decreases the electrical impedance while increasing the charge capacity of the electrode. To assess these changes, we measure the electrical properties of the diffuse polymer electrode networks by performing Electrical Impedance Spectroscopy (EIS) and Cyclic Voltammetry (CV) as described in Examples 1 and 2.

Example 5

All Polymer Electrodes

In certain embodiments, Polymer wires/electrodes are non-metallic, non-ceramic, and do not contain metalloids (e.g. Silicon) or alloys. Polymer electrodes are comprised of a conducting polymer or combinations of conducting polymers and non-conductive polymers or hydrogels juxtaposed in specific configurations resulting in an electrode lead that can be used in place of "normal" metal electrodes or wires. In some embodiments, the polymer electrode may also contain carbon or carbon nanotubes. All polymer wires/electrodes offer at least 2 major advantages over more traditional metal electrodes. Polymer electrodes can be used in any situation in which it would be unfavorable, dangerous, or impossible to use metal such as in the presence of a magnetic field (e.g. MRI scans of individuals with implanted devices that contain metal electrodes devices or bioprosthetics). Secondly, polymer electrodes can be created several ways from a diversity of substrates and materials and are highly adaptable and can be readily tailored for specific, diverse applications from chemical sensing to tissue engineering to the next generation of laboratory and scientific testing/analysis equipment. In addition the polymers comprising these polymer electrodes can be prepared to contain or release bioactive agents which can facilitate electrode (or device) function and communication/integration at the interface between the electrode and the electrolyte.

Applications in which electrodes must be deployed in aqueous environments will likely benefit most from use of all polymer wires. This is due in part to the fact that the function of metal wires is often compromised in aqueous environments as well as the fact that the function of all polymer electrodes is in part dependent on and can be enhanced by interaction with electrolytes in the aqueous environments. In addition specific ionic interactions between the polymer electrode and the electrolyte can be exploited to facilitate the function of the device to which the polymer electrode is communicating-similar flexibility is not inherent to more traditional metal electrodes. Four possible designs for all polymer electrodes are presented in the accompanying figures.

Methods and Materials. A non-degradable tubular polymer container 0.5 cm-10 cm in length having a diameter of 1-5 cm is sterilized. Polymeric micro/nano fibers, 0.5-9 cm in length are aligned inside the container. Solution of EDOT monomer and appropriate dopant e.g. poly(styrene sulfonate) is placed in the container and the fibers are connected via a lead to a source of current. Polymerization of the conducting monomer is carried out as described in Examples 1 & 2. Excess reagents are removed leaving behind and the conductive polymer coated fibers. An electrical connection is affixed at one end of the container. Hydrogen can optionally be poured into the container to coat and surround the conductive micro/nano fibers. The hydrogel can optionally contain living cells, for example stem cells or biodegradable micro/nano particles containing bioactive agents, for example drugs, pharmaceuticals, enzymes growth factors and the like. The container can be implanted into the bioelectrode implantation site and connected to a power source via a polymer lead with a metal or conducting polymer.

Polymer Electrode characterization/measurement of functionality & effectiveness. To assess whether the all polymer electrodes are electrically active, functional electrodes, the electrodes are tested as described in Examples 1-3.

All polymer electrodes can be implemented as special leads that can be attached to devices via traditional metal wires. Therefore it is necessary to have a device and its various leads/wires available for connection to the all polymer electrodes/leads. We expect that a diversity of devices will be compatible with these all polymer electrodes/leads; bio/ion/chemical sensors, "lab-on-chip" devices, implanted biomedical devices, and bioprosthetics components.

Example 6

Diagnostic and "Lab-On Chip" Devices

Conducting polymer-based coatings can be applied to "lab-on-chip" electrodes via electrochemical polymerization of conducting monomers described by various embodiments of the present teachings. Various biological components can be incorporated into the conducting polymer matrix during the electrochemical polymerization process. These components include but are not limited to antigens, antibodies, receptors, natural or synthetic membranes containing proteins, synthetic micro or nanoparticles that are coated with antibodies, antigens, or ligand-specific surface coatings (e.g. peptides, nucleic acids, chemicals, receptors, proteins), live cells or organisms (e.g. bacteria, viruses), enzymes, synthetic or natural polymers/macromolecules, and multi-protein complexes.

These biological components are incorporated into the conducting polymer matrix during the electrochemical polymerization process using one of the following methods; 1) the agent is added directly to the monomer solution (may also contain ionic dopants and counterions), 2) the agent is deposited on or adhered to the surface of the bare electrode, 3) the agent is injected directly near the electrode sites once the electrochemical polymerization process is underway. In all of these situations, the total surface area of the microelectrodes is calculated, the microelectrodes of the device are bathed in monomer solution, and then electrical current is applied (0.5-1.5 uA/mm$^2$) for durations typically ranging from 30 seconds to 30 minutes. The monomer polymerizes around the biological components entrapping them in a nanoporous polymer matrix (allows ion flow and mass transport/diffusion through polymer matrix) that forms directly and exclusively on top of the microelectrode sites.

Characterization/measurement of functionality & effectiveness of conducting polymer-based coatings for "lab-on-chip" electrodes: The electrical properties of conducting polymer-based coatings on "lab-on-chip" electrodes are assessed using the same methods described for other conducting polymer (e.g. PEDOT)-based bioelectrode coatings described herein (specifically, live cell bioelectrodes, and cell templated bioelectrodes). The sensing or stimulating functions of the PEDOT-based coating on "lab-on-chip" electrodes can be assessed uniquely within the context of each "lab-on-chip" device. For example: a "lab-on-chip" device senses the presence of a specific antigen through the use of antibodies embedded within the PEDOT matrix. When the pathogen is present, antigens on the pathogens surface bind the antibodies within the polymer matrix and thus increase the electrode resistance and/or induce an alteration in surface charge of the conducting polymer. Increased resistance and/or a change in polymer surface charge are detected by the underlying electrode which transmits this information to the device so that the device can report successful detection of the antigen. In this way, the functionality and effectiveness of the PEDOT-based sensor/coating on the "lab-on-chip" electrodes can be assessed using multiple parameters that depend on both the electrical properties of the electrode coatings as well as the bioactive/sensing properties of the coatings. It is preferred that the sensitivity and specificity of the pathogen detecting capabilities are measured and compared to existing/more traditional methods of detecting the pathogen of interest.

To best exploit both the unique electrical properties of conducting polymers and the specific detecting functions provided by the biological components incorporated into the conducting polymer matrix, a variety of electrochemical analyses will be used to enable detection of binding events between the biological components in the conducting polymer matrix and the "target analyte" in the sample solution. This includes but is not limited to potentiometry, amperometry, cyclic voltammetry, capacitative coupling, and/or electrical impedance spectroscopy. The specific electrochemical analysis to be used by a device will depend on which type of biological component is present in the conducting polymer matrix and which target analyte in the sample solution is to be detected. The various electrochemical analysis methods are described below and examples (within the context of a conducting polymer matrix, "lab-on-chip" application) are given for their use.

Potentiometry: In this electrochemical analysis method, voltage or potential is measured under zero current flow conditions using a 2-electrode system, a cathode and an anode. The voltage difference between the cathode and the anode is considered the potential of the electrochemical cell. For lab on chip device applications, the conducting polymer matrix containing the biological component is coated on the first electrode substrate (usually the cathode). The sample solution is bathed across the first and second electrodes and the target analyte in the sample solution can bind to the biological component in the conducting polymer matrix. This event elicits a change in surface energy of the conducting polymer matrix and underlying cathode by altering the species of molecules (and their charges) at the first electrode surface as well as by possibly inducing conformational changes in either or both the biological component and the target analyte which alters charge distribution over the bound/complexed agents. The surface energy change causes a voltage difference between the anode and the cathode. This induces a positive detection response from the lab on chip device.

Amperometry: In this electrochemical analysis method, the difference in electrical current between 2 electrodes is measured while constant voltage is applied to one of the electrodes (considered the working electrode). Like potentiometry, this method can also be used to detect changes in conducting polymer matrix/electrode surface energy and similar concepts can be applied.

Voltammetry (Linear Sweep and Cyclic): A 3-electrode set-up is used for this electrochemical analysis method, the working electrode, counter electrode, and reference electrode. The voltage (relative to the reference electrode) is swept at a constant rate from one voltage to another and the change in electrical current is measured throughout the assay. For linear sweep voltammetry, the voltage is swept from a low potential (0.5 V to 5 V) to some higher potential whereas for cyclic voltammetry (CV) a triangular waveform is used in which the voltage is swept from some negative potential to a positive potential then back to the negative potential (−1V to +1V to −1V). CV is commonly used to measure the redox potentials of chemicals and interfaces in electrolyte solutions. For lab-on-chip device applications, CV can be performed on the first electrode substrate coated with the conducting polymer matrix containing the biological component before and after exposure to the sample solution containing the target analyte. The bound/complexed agents will display a unique CV scan with redox peaks(s) located at different positions than what is characteristic of the conducting polymer matrix prior to exposure to the sample solution or the binding event. Due to its ability to detect redox activity, the CV scan can be used for 2 additional analyses; 1) real-time detection of formation of a binding event(s) between the complimentary molecules at the conducting polymer matrix and 2) detection of degradation or alterations in the electrical or physical stability of the conducting polymer matrix.

Electrical impedance spectroscopy (EIS): Similar to voltammetry, a 3-electrode set-up is used for EIS. In this method alternating current (AC) is applied at a series of increasing frequencies (Hz) and the impedance (Z) is recorded. Z is similar to resistance in a DC environment but in this case because AC the element that would be essentially equivalent to resistance in Ohms law is Z which is determined by the relationship between its 3 components, resistance, capacitance, and inductance. For lab-on-chip device embodiments, the impedance of the first electrically conductive substrate coated with the conducting polymer containing the biological component is measured before and after exposure to the sample solution. Specific binding of the target analyte in the sample solution to the biological component in the conducting polymer matrix will increase the impedance and alter the phase angle of the impedance, and this will elicit a positive detection response from the device. Like CV, EIS can also be used to measure other aspects of interaction between the electrode and the solution. For example, a specific binding event between the complimentary biological component-target analyte will be associated with a distinct EIS profile whereas non-specific binding of agents in the sample solution to the conducting polymer matrix and electrode will also increase impedance but this will have a unique pattern that is distinguishable from that of a specific binding event.

Both potentiometry and amperometry can be simple, one-step analyses that require little programming or battery power which is an advantage. Therefore the electrochemical analysis method selected can be based on which biological component is to be used as well as on what kinds of sample solutions the electrode will be exposed to. For example, a lab-on-chip device that employs potentiometry would be preferable for an application in which it is desired to detect nucleic acids from a laboratory sample that is otherwise comprised of a saline solution. In contrast, potentiometry is less selective. For detecting antibodies in blood or serum it would be preferable to design a lab-on-chip device that employs CV or EIS electrochemical analyses.

Conducting polymer-based coatings are applied to electrodes on a device, thus it is necessary that the electrode substrate(s) of the device are accessible for polymerization procedures. In addition, because the conducting polymer coatings provide enhanced electrode sensitivity and charge transfer capacity it is preferable that both the hardware and software associated with device function are capable of transmitting and interpreting information coming from the lab on chip device.

The description of the present disclosure is merely exemplary in nature and, thus, variations that do not depart from the gist of the invention are intended to be within the scope of the invention. Such variations are not to be regarded as a departure from the spirit and scope of the invention.

What is claimed is:

1. A biologically integrated bioelectrode device comprising:

(i) a first electrically conductive substrate;

(ii) a biological component; and (iii) a conductive polymer electrically coupling said first electrically conductive substrate to said biological component to collectively define a bioelectrode, said bioelectrode transmitting or receiving an electrical signal between the first electrically conductive substrate and one of said biological component and conductive polymer, said conductive polymer comprising a surface formed by a template biological component, wherein most or all of said template biological component is removed from said surface, and said biological component is coupled to said surface.

2. The biologically integrated bioelectrode device according to claim 1, wherein said biological component includes one or more of a tissue, organic living cell, a cellular constituent or combinations thereof.

3. The biologically integrated bioelectrode device according to claim 2, wherein said organic living cell is selected from the group consisting essentially of natural or recombinant eukaryotic cells and prokaryotic cells.

4. The biologically integrated bioelectrode device according to claim 3, wherein said eukaryotic cells is selected from the group consisting essentially of cardiac cells, neural cells, muscle cells, stem cells, stromal cells, hematopoietic cells and combinations thereof.

5. The biologically integrated bioelectrode device according to claim 4, wherein said neural cells comprise neurons.

6. The biologically integrated bioelectrode device according to claim 2, wherein said cellular constituent is selected from the group consisting essentially of a membrane, an organelle, an ion-channel, a lipid bi-layer, a receptor, an enzyme, a protein, an antibody, an antigen, a nucleic acid, a carbohydrate, and combinations thereof.

7. The biologically integrated bioelectrode device according to claim 1, wherein said bioelectrode further comprises at least one hydrogel in proximate contact with said conductive polymer.

8. The biologically integrated bioelectrode device according to claim 7, wherein said hydrogel further comprises a bioactive substance.

9. The biologically integrated bioelectrode device according to claim 1, wherein said conductive polymer is chosen from the group consisting essentially of copolymers and homopolymers of EDOT, pyrrole, and their functionalized derivatives and copolymers, polyanilines, salt of polyaniline, polyacetylenes, polythiophenes, a poly(3,4-ethylenedithiathiophene), polymer blends thereof, hybrid polymer-metal materials and combinations thereof.

10. The biologically integrated bioelectrode device according to claim 9, wherein the polymers of EDOT and pyrrole is chosen from the group consisting essentially of poly(3,4-ethylenedioxythiophene) (PEDOT), poly(pyrrole), their derivatives and combinations thereof.

11. The biologically integrated bioelectrode device according to claim 1, wherein said conductive polymer is polymerized around said biological component and said first electrically conductive substrate.

12. The biologically integrated bioelectrode device according to claim 1, wherein said first electrically conductive substrate contains a conductor chosen from the group consisting essentially of gold, silver, platinum, palladium, tungsten, nickel, titanium, indium tin oxide, copper, carbon, carbon black, carbon fiber, carbon paste, graphite, doped silicon, ceramic, conductive polymer, and combinations thereof.

13. The biologically integrated bioelectrode device according to claim 1, wherein said bioelectrode further comprises one or more dopants participating in polymerization of the conducting polymer and transmitting or receiving said electrical signal between the first electrically conductive substrate and said conductive polymer.

14. The biologically integrated bioelectrode device according to claim 1, further comprising a second electrically conductive substrate coupled to the biological component.

15. The biologically integrated bioelectrode device according to claim 14, further comprising an electrical source of power or current operable to communicate with said first and second electrically conductive substrates and the biological component using one or more electrical signals.

16. The biologically integrated bioelectrode device according to claim 1, wherein said template biological component includes one or more of a tissue, organic living cell, a cellular constituent or combinations thereof.

17. The biologically integrated bioelectrode device according to claim 16, wherein said organic living cell is selected from the group consisting essentially of natural or recombinant eukaryotic cells and prokaryotic cells.

18. The biologically integrated bioelectrode device according to claim 16, wherein said cellular constituent is selected from the group consisting essentially of a membrane, an organelle, an ion-channel, a lipid bi-layer, a receptor, an enzyme, a protein, an antibody, an antigen, a nucleic acid, a carbohydrate, and combinations thereof.

19. The biologically integrated bioelectrode device according to claim 17, wherein said eukaryotic cells is selected from the group consisting essentially of cardiac cells, neural cells, muscle cells, stem cells, stromal cells, hematopoietic cells and combinations thereof.

20. The biologically integrated bioelectrode device according to claim 19, wherein said neural cells comprise neurons.

21. A biologically compatible electrode comprising:

(a) an electrically conductive substrate;

(b) a coating on at least some portion of at least one surface of said electrically conductive substrate, the coating comprising:

a biological component, and (ii) a conductive polymer comprising a surface formed by a template biological component, wherein most or all of said template biological component is removed from said surface, and said biological component is coupled to said surface.

22. A biocompatible and biomimetic coating for an electrically conductive substrate comprising:

(a) an electrically conductive polymer, and (b) a biological component, wherein the electrically conductive polymer comprises a surface formed by a template biological component, wherein most or all of the template biological component is removed from the surface, and the biological component is coupled to the surface.

23. A device comprising a biocompatible and biomimetic coating according to claim 17, wherein said device comprises a microelectrode array, lab on chip device, or target analyte detection device.

24. A method of electrically detecting a transfer of electrical signals between living cells, comprising the steps:

applying a voltage or current across said first electrically conductive substrate of the bioelectrode device of claim 1 and a second electrically conductive substrate, thereby inducing a voltage or current across said conductive polymer, said second electrically conductive substrate being electrically coupled to said device and a power source; and detecting the transfer of electrical signals with said bioelectrode device.

25. The method according to claim 24, wherein said biological component is chosen from the group consisting essentially of cardiac cells, neural cells and muscle cells.

26. The method according to claim 24, wherein the detecting step comprises detecting the transfer of electrical signals wherein said signal is selected from the group consisting essentially of impedance, resistance, capacitance, inductance, and current.

27. The method according to claim 24, wherein said conductive polymer is chosen from the group consisting essentially of copolymers and homopolymers of EDOT, pyrrole, and their functionalized derivatives and copolymers, polyanilines, salt of polyaniline, polyacetylenes, polythiophenes, a poly(3,4-ethylenedithiathiophene), polymer blends thereof, hybrid polymer-metal materials and combinations thereof.

28. The method according to claim 27, wherein the copolymers and homopolymers of EDOT and pyrrole is chosen from the group consisting essentially of poly(3,4-ethylenedioxythiophene) (PEDOT), poly(pyrrole), and combinations thereof.

29. A biologically integrated bioelectrode device comprising conducting polymer in proximate contact with a first electrically conductive substrate and at least one biological component formed by the steps of:

(a) contacting a template biological component with said first electrically conductive substrate, said first electrically conductive substrate chosen from the group consisting essentially of metals, ceramics, carbon, conductive polymers and combinations thereof so as to form a biologically interfaced electrode;

(b) immersing said biologically interfaced electrode in a solution comprising conducting monomer and dopant; and (c) polymerizing said monomer around said biologically interfaced electrode by inserting a second electrically conductive substrate into said solution of step (b) and applying galvanostatic or potentiostatic current to said first and second electrically conductive substrates for a sufficient time to coat the biologically interfaced electrode with conductive polymer;

(d) removing most or all of said template biological component from the conductive polymer to expose a surface formed by the template biological component; and (e) contacting the at least one biological component with said surface to form the biologically integrated bioelectrode device.

* * * * *

UNITED STATES PATENT AND TRADEMARK OFFICE

CERTIFICATE OF CORRECTION

PATENT NO. : 8,005,526 B2
APPLICATION NO. : 11/512479
DATED : August 23, 2011
INVENTOR(S) : David C. Martin et al.

It is certified that error appears in the above-identified patent and that said Letters Patent is hereby corrected as shown below:

Column 1, line 21, “relates” should be --relate--.

Column 1, line 25, “relates” should be --relate--.

Column 2, line 54, after “substrate” insert --,--.

Column 5, line 67, after “arrays” insert --,--.

Column 8, line 2, “polymer” should be --polymers--.

Column 8, line 7, “attach” should be --attached--.

Column 9, line 34, after “poly(3,4” insert -- - --.

Column 9, line 49, “pdoping” should be --p-doping--.

Column 10, lines 44-45, after “prokaryotic cells” insert --)--.

Column 11, line 56, “CPU’s” should be --CPUs--.

Column 12, line 32, after “FIG. 1)” insert --.--.

Column 12, line 47, after “stability” delete “under”.

Column 14, line 4, “Biolectrodes” should be --Bioelectrodes--.

Column 15, line 22, “with in” should be --within--.

Column 15, line 26, “Panel” should be --Panels--.

Signed and Sealed this
Tenth Day of January, 2012

David J. Kappos
*Director of the United States Patent and Trademark Office*

Column 16, line 7, “place” should be --placed--.

Column 16, line 38, “polymer” should be --Polymer--.

Column 16, line 53, “electrodes” should be --electrode--.

Column 17, line 66, after “impedance”, delete “of the”.

Column 18, line 16, “stem cells etc)” should be --stem cells, etc.)--.

Column 18, line 46, “in to” should be --into--.

Column 19, line 21, after “substrate” insert --,--.

Column 20, line 42, after “regeneration” delete “and”.

Column 21, lines 36-37, “complimentary” should be --complementary--.

Column 22, line 12, after “plastics” insert --,--.

Column 22, lines 23-24, “elelctrochemical” should be --electrochemical--.

Column 23, line 5, after “teachings” insert --.--.

Column 23, line 11, after “device” delete “that”.

Column 23, line 14, after “reaction” delete “that”.

Column 23, line 51, “an biologic” should be --a biologic--.

Column 25, line 47, After “electrode” insert --.--.

Column 26, line 2, “Nanoscope IIII” should be --Nanoscope III--.

Column 26, line 19, After “Eugene” insert --,--.

Column 33, line 5, “RS” should be --$R_s$--.

Column 33, line 49, “Au/P” should be --Au/Pd--.

Column 38, line 11, after “Systems” insert --,--.

Column 38, line 19, “CO2” should be --$CO_2$--.

Column 38, line 30, “CO2” should be --$CO_2$--.

Column 39, line 60, “electrodes” should be --electrode--.

Column 40, line 33, “enzymes” should be --enzyme--.

Column 40, line 52, “Lab-On Chip” should be --Lab-On-Chip--.

Column 42, lines 2-3, “lab on chip” should be --“lab-on-chip”--.

Column 42, line 17, “lab on chip” should be --“lab-on-chip”--.

Column 42, line 38, “lab-on-chip” should be --“lab-on-chip”--.

Column 42, line 43, “peaks(s)” should be --peak(s)--.

Column 42, line 48, “complimentary” should be --complementary--.

Column 42, line 60, “lab-on-chip” should be --“lab-on-chip”--.

Column 43, line 4, “complimentary” should be --complementary--.

Column 43, line 16, “lab-on-chip” should be --“lab-on-chip”--.

Column 43, line 21, “lab-on-chip” should be --“lab-on-chip”--.

Column 43, lines 30-31, “lab on chip” should be --“lab-on-chip”--.

Column 45, line 11, Claim 21, before “a biological component” insert --(i)--.

Column 45, line 29, Claim 23, “lab on chip” should be --“lab-on-chip”--.